United States Patent [19]
Callicrate

[11] Patent Number: 5,843,095
[45] Date of Patent: Dec. 1, 1998

[54] METHOD AND SYSTEM FOR RAISING AND CASTRATING CATTLE

[76] Inventor: Michael P. Callicrate, Rt. 2, Box 133, St. Francis, Kans. 67756

[21] Appl. No.: 938,326

[22] Filed: Sep. 26, 1997

Related U.S. Application Data

[63] Continuation-in-part of Ser. No. 414,638, Apr. 3, 1995, Pat. No. 5,681,329.

[51] Int. Cl.⁶ .................................................. A61B 17/12
[52] U.S. Cl. ............................... 606/141; 606/141; 426/1
[58] Field of Search ..................................... 606/135, 138, 606/139, 140, 141, 151, 157, 113; 119/174, 51.01; 426/1, 2

[56] References Cited

U.S. PATENT DOCUMENTS

| | | |
|---|---|---|
| 612,569 | 10/1898 | Moscrop . |
| 1,615,124 | 1/1927 | Lespinasse ............................... 606/135 |
| 1,885,945 | 11/1932 | Ransy . |
| 2,124,404 | 8/1938 | Snyder ..................................... 606/140 |
| 2,487,425 | 11/1949 | Collins . |
| 2,642,057 | 6/1953 | Watkins ..................................... 124/17 |
| 3,080,867 | 3/1963 | Eichinger ................................. 606/113 |
| 3,547,124 | 12/1970 | Fergusson . |
| 3,687,138 | 8/1972 | Jarvik . |
| 3,726,278 | 4/1973 | Scott . |
| 3,813,983 | 6/1974 | Paul ........................................... 81/469 |
| 3,915,150 | 10/1975 | Ray ............................................. 128/1 |
| 4,220,155 | 9/1980 | Kimberling et al. . |
| 4,335,490 | 6/1982 | Teachout ................................. 24/17 B |
| 4,569,324 | 2/1986 | Garcia ................................... 124/20.01 |
| 4,572,179 | 2/1986 | Tietelbaum et al. . |
| 4,682,716 | 7/1987 | Morellini . |
| 4,691,704 | 9/1987 | Wadsworth . |
| 4,721,169 | 1/1988 | Nagasawa et al. ......................... 81/469 |
| 4,966,057 | 10/1990 | Koppatsch ................................. 81/469 |
| 4,966,600 | 10/1990 | Songer et al. ............................. 606/74 |
| 4,986,369 | 1/1991 | Fushiya et al. ........................... 81/467 |
| 5,127,389 | 7/1992 | Magnuson ............................. 124/20.01 |
| 5,163,948 | 11/1992 | Kummer .................................. 606/151 |
| 5,188,637 | 2/1993 | Wadsworth ............................. 606/151 |
| 5,190,560 | 3/1993 | Woods et al. ............................ 606/137 |
| 5,279,276 | 1/1994 | Nagel et al. ............................ 124/20.1 |
| 5,282,825 | 2/1994 | Muck et al. ............................. 606/203 |
| 5,459,905 | 10/1995 | Voyre ....................................... 24/17 B |
| 5,520,702 | 5/1996 | Sauer et al. ............................. 606/148 |

FOREIGN PATENT DOCUMENTS

| 1201722 | 9/1965 | Germany .............................. 124/20.1 |
|---|---|---|

OTHER PUBLICATIONS

Food Sci. & Tech. Abs, FSTA IFIS Publishing, Dec. 1994.
CAB Abstracts, CAB International, Dec. 1996.
Biosis Previews, Biosis, Dec. 1996.

*Primary Examiner*—Michael Buiz
*Assistant Examiner*—Vikki Trinh
*Attorney, Agent, or Firm*—Sheridan Ross P.C.

[57] ABSTRACT

An apparatus and method for use in raising cattle, and in particular bulls, wherein bulls are:

(a) fed a particularly nutritious liquid having a distinctive odor prior to weaning;

(b) fed a combination of this liquid and conventional feed after weaning in a feedlot;

(c) castrated using a ligation tool that provides a ligating tension to endless elastomeric ligation bands wherein the tool indicates the tension applied to such ligation bands; and (d) treated for infection prevention at least around the time of castration.

Accordingly, cattle growth is accelerated due to enhanced nutrition, reduction in disease and a reduction in the stress upon the cattle. Furthermore, late castration of bulls (at approximately 5 to 14 months) is employed, wherein the tool of (c) provides a substantially stress-free ligation technique. Moreover, the meat produced from the cattle processed using the present invention has superior cutability characteristics.

21 Claims, 19 Drawing Sheets

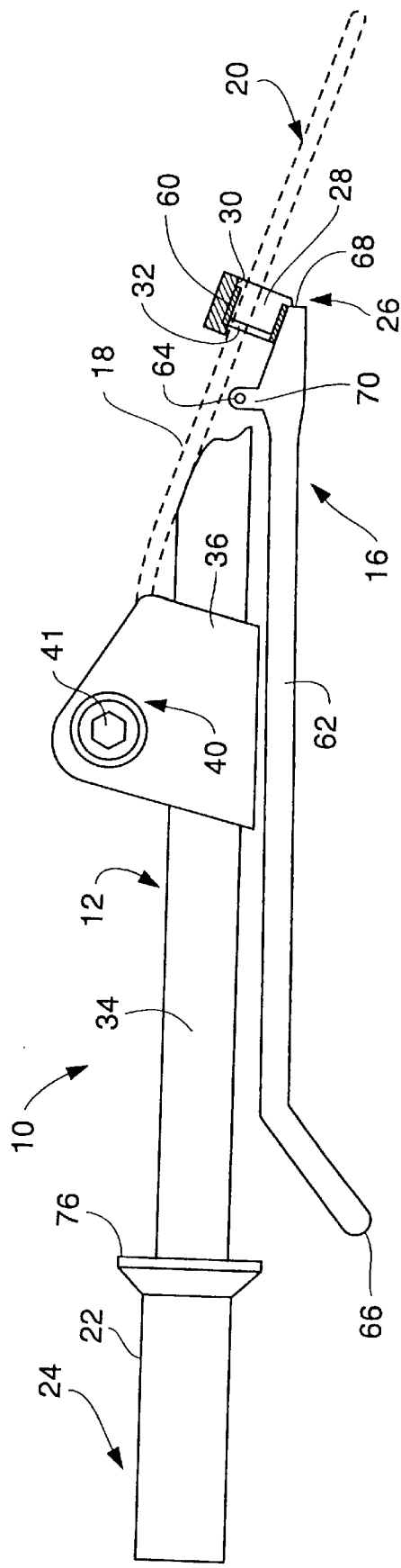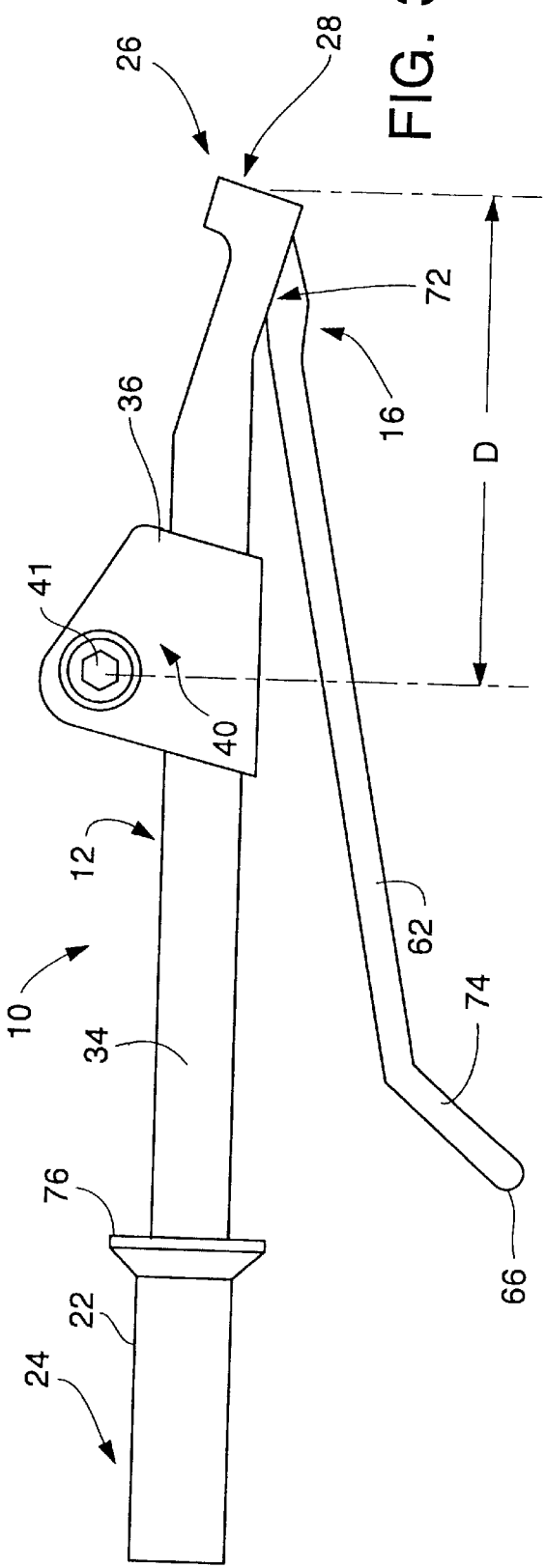

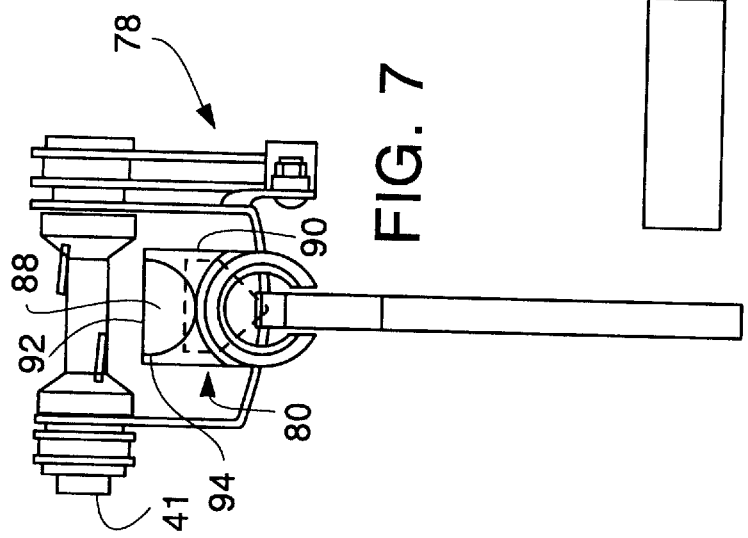
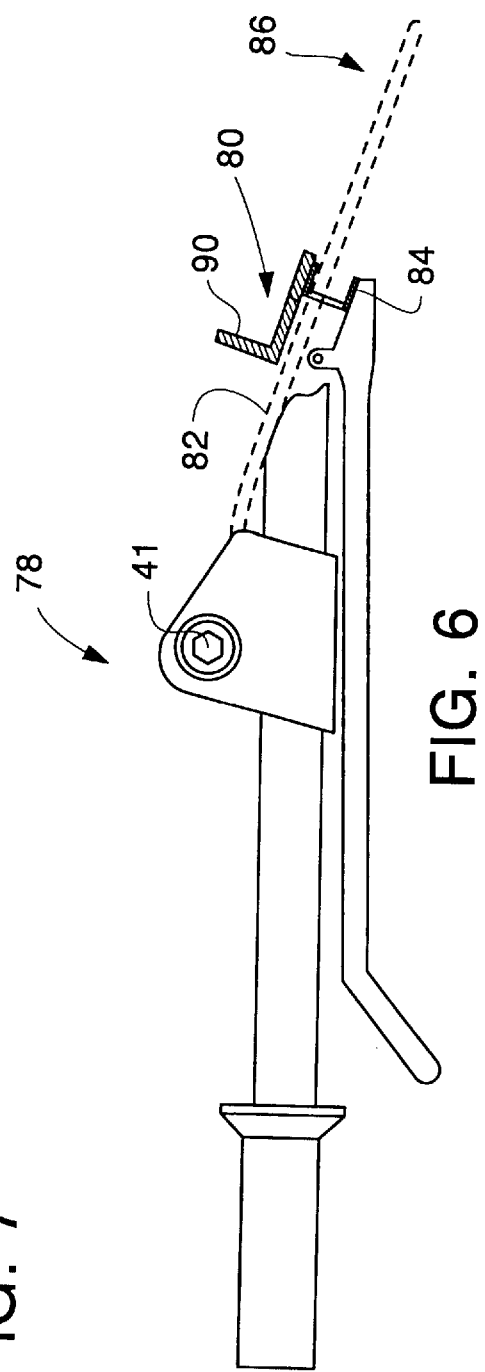
FIG. 7
FIG. 6

METHOD AND SYSTEM FOR RAISING AND CASTRATING CATTLE

CROSS-REFERENCE TO RELATED APPLICATIONS

The present application is a continuation-in-part of U.S. patent application Ser. No. 08/414,638, filed Apr. 3, 1995 entitled METHOD AND APPARATUS FOR CASTRATION USING AN ENDLESS ELASTIC LOOP. This related application is incorporated herein by reference in its entirety.

FIELD OF THE INVENTION

This invention relates in general to methods and apparatuses for raising meat producing cattle to achieve superior growth of such animals and, in particular, relates to a method and apparatus for weaning, feeding and castration of cattle to improve the profitability of a cattle raising operation.

BACKGROUND OF THE INVENTION

A common method for the removal of a body part is ligation. Ligation is a process in which a band or cord is fastened to the body part to be removed in order to constrict it, thus cutting off the supply of blood and systemic support. The body part thereafter atrophies and drops away from the body. Ligation has been used for many purposes including castration and the removal of horns, tails or other body parts from animals.

Ligation has a number of advantages over surgical procedures for such applications. First, ligation has a safety advantage in that the animal normally does not become susceptible to infection. For example, in the case of castration of bulls, a period of about two weeks to a month typically passes between the time that the ligature is attached to the scrotum and the time that the scrotum drops off. During this time the area adjacent the ligature heals, thus reducing the likelihood of infection. Another advantage of ligation is that ligation can be performed quickly by non-expert personnel, thereby reducing costs. In addition, when the ligature is sufficiently tight, ligation can generally be performed with little stress on the animal because the body part numbs quickly after the blood supply is cut off.

According to one conventional method of ligation, an endless loop of elastic band is stretched to encircle a body part and is used to cut off the blood supply to the body part to be removed. Because the band is endless, the band must be stretched to open it up a sufficient amount so that it can be positioned by passing the band loop over the body part as disclosed in U.S. Pat. No. 4,527,179. This conventional method has the disadvantage that it is difficult to attach the ligature band such that it is sufficiently tight. For example, when an endless band is used to castrate bulls, the band must be stretched to pass over the scrotal sac and its contents and then released to engage the sac at the desired position. The tightness of the band when positioned is therefore limited by the band's elasticity. In addition, because an endless ligature band generally cannot be tightened, the size of the band loop can only be roughly matched to a particular application. That is, the band is usually selected from a limited number of discrete band sizes. Because of the difficulty in tightening conventional endless bands, such bands may fail to sufficiently cut off the blood supply resulting in prolonged stress to the animal and an increased likelihood of swelling and/or infection. In addition, there is a greater chance that the animal will intentionally or unintentionally displace a loose band.

Another ligation method is disclosed in U.S. Pat. No. 4,691,704. A loop of a ligature elastomeric band is formed around the body part to be ligated, and then an end portion of the band is attached to a tightening rod. The tightening rod can then be retracted in a substantially linear fashion by successive pulls on a trigger mechanism, thereby tightening the loop. However, the process of tightening the loop through successive pulls on the trigger mechanism is time consuming and the animal must therefore be restrained for a longer period of time. In addition, the tension which can be imparted to the band, and the tightness of the loop, are limited by the hand strength of the user. Moreover, relatively large frictional and abrasive forces are exerted on the band where the band is attached to the tightening rod, thereby increasing the likelihood of damage to the elastomeric material causing breakage before the desired tension is achieved. Furthermore, the attachment of the end portions of the band can be time consuming and thus impede the speed at which cattle or other livestock can be processed. Additionally, due to the design of the ligature tool, an operator is limited in the extent a band can be tightened. Once an operator has fully retracted the tightening rod, the loop's tightness cannot be increased.

The inability to achieve relatively quick and complete occlusion of both venous and arterial pressure within the body part being ligated may result in the venous pressure alone being shut off, thereby permitting the stronger arterial pressure to fill the body part with blood. This, in turn, can lead to swelling of the body part and failure of the ligation process, causing consequential pain to the animal.

Accordingly, it would be advantageous to provide a ligation tool that can attain a given tension on any elastomeric band without being limited by tool design. It would be further advantageous for the ligation tool to provide an indicator of the tension in the band so that an operator can be assured that an effective amount of ligating tension has been placed on the band.

Additionally, the cattle raising industry has experienced decreased profits due to an imbalance between meat prices and the overhead involved in the raising of cattle. This is at least in part due to conventional cattle raising practices where young male calves are castrated and branded at an early age, thus depriving such calves of natural hormones that promote growth. Moreover, cattle can become highly stressed at various periods, causing slow growth, loss in weight and/or a lower quality or grade of meat. For example, cattle may become especially stressed when the cattle experience any of the following events: being abruptly weaned, provided with unfamiliar surroundings or feed, and castrated, especially in a later period of their life (e.g., at six months to around one year old).

Moreover, cattle raising overhead has increased due to the practice of early castration of bulls followed by subsequent provision to such castrated animals (i.e., steers) with hormone supplements to increase growth and promote weight gain. Thus, not only do such steers experience a reduced growth in comparison with (uncastrated) bulls, but the ratio of lean meat to fat is decreased, thereby providing a lower quality of meat.

Accordingly, it would be advantageous to provide a cattle raising management program that reduces the stress in cattle related to the above-mentioned events and also to reduce or eliminate the need for hormone supplements to be provided to steers. Further, it would also be advantageous to provide a cattle raising management program that decreases the cattle raising overhead by accelerating the growth of cattle so that the age by which cattle can be profitably slaughtered is decreased.

SUMMARY OF THE INVENTION

The present invention discloses a method and apparatus for ligation which avoids or alleviates the problems discussed above. The present invention allows a ligature band to be tightly attached to an animal body part thereby reducing the likelihood of swelling, infection and/or prolonged stress to the animal. The present invention also allows the band to be tightened quickly thereby reducing the length of time that the animal must be restrained.

According to one aspect of the present invention, a method and apparatus for ligation is provided. The method includes the steps of forming a loop about the body part with a band of ligature material and winding the band to tighten the loop. Preferably, the band is tightened by securing the band to a spool and then rotating the spool to wind the band. After the loop is tightened, the loop can be secured by crimping a grommet so that the band is secured therein.

A separate aspect of the present invention relates to a method and apparatus for using a preformed endless loop to sever animal parts. Use of an endless ligation loop eliminates the conventional practice of using a linear length of banding material to form a loop around a body part and avoids the subsequent need to attach the respective ends of the band to a means for pulling the band to tighten the loop. Furthermore, use of a pre-formed loop (i.e., formed prior to insertion of any band material into a ligation device) eliminates the need for cumbersome lengths of ligation material used in conventional ligation operations and enables an operator to slip pre-formed loops around a belt, into a carrying case, etc., thus facilitating easy access to such loops when performing multiple ligation procedures. Moreover, use of pre-formed loops having pre-attached grommets ensures that a loop is never tightened without a grommet first being in place. The likelihood of losing the grommet is also reduced and the preformed endless loop may be inserted in the tool and attached to a means for pulling in a more efficient manner. The pre-formed loop having a grommet pre-attached to the loop, (preferably to form an hour-glass shaped loop) is useful not only with the winding tool disclosed herein, but is also useful with prior art devices, such as the "caulking gun-type" device described by Wadsworth, U.S. Pat. No. 4,691,704.

Moreover, it is an aspect of the present invention that such pre-formed endless loops may be formed from a length of elastomeric band without the use of additional components for tying the ends of the length together. In particular, it has been discovered by the inventor that by providing a passageway through a thickness of the elastomeric band (e.g., by puncturing) and expanding the passageway sufficiently, so that one of the band ends can be inserted therethrough, that when the passageway is allowed to constrict about the inserted end, a loop is obtained that can be effectively used by the ligation tool of the present invention.

A tool constructed in accordance with an embodiment of the present invention includes a receiving device for receiving a band of ligature material, wherein the band forms a loop external to the receiving device. A winding assembly is interconnected to the receiving device such that the loop is tightened by winding the band.

Preferably, the winding assembly includes a spool that facilitates the securing of a band thereabout as the spool is rotated. A ratchet mechanism can be employed to provide for one way rotation of the spool. In one embodiment, the tool is operated by pneumatic or electrical motors or by power tools which function to wind the band around the spool to achieve a desired loop tightness or tension. In a related embodiment, the motor or power source used to wind the tool is recessed within the handle portion of the tool and engages a worm gear or other similar mechanism to rotate the winding spool. The tightness of the loop can be modified by adjusting either the pneumatic/electrical winding device so that winding of ligature material ceases at a predetermined tension, or by providing a clutch mechanism on the tool itself. The winding assembly may rotate in a direction perpendicular to the longitudinal axis of the tool effectively shortening the endless loop and applying pressure around the selected body part of the animal.

In another embodiment of the ligation tool of the present invention, the tool is provided with a tensioning indicator that indicates the tension applied to an elastomeric loop during a ligation procedure. Thus an operator of this embodiment of the tool can be assured that an effective ligation tension is provided to the loop. Moreover, in one embodiment of the tool, the tension indicator is provided by a compressible tool body, wherein the amount of compression indicates a corresponding tension on the loop or band. The compressible tool body may be provided by telescoping tool body segment, wherein one tool body segment slidably moves or compresses as an insert within an outer tool body segment. Further, a compression spring may be used to provide resistance against compression forces urging the inserted body segment further into the outer tool body segment. Thus, by calibrating the extent of compression of the compression spring for various degrees of compressive force, a loop tension indicator can be provided as one or more markings on either the inner or the outer tool body segment.

In a preferred embodiment, the tool includes a lever which is biased against the grommet located in a receptacle in the receiving end of the tool. The pressure exerted by the lever prevents the grommet from inadvertently being mispositioned prior to and during the operation of the tool. Furthermore, when sufficient tension is put on the endless loop and consequent pressure is applied to the body part to be severed, the lever is used to deform the grommet upon and/or around the endless loop to secure the loop around the animal's body part. When it is desired to release the tool from the ligature material, the lever position is reversed.

In another aspect of the present invention, the ligation method and apparatus of the present invention may be used with a novel method for raising cattle, and more particularly bulls, wherein there is an increase in the quantity and/or quality of meat produced, as well as a reduction in the practice of administering hormonal supplements to steers. That is, this aspect of the present invention combines the use of ligation as disclosed herein within the context of a novel cattle raising management program. In particular, the modifications provided by the present invention include steps for reducing cattle stress and sickness during: weaning, placing calves in unfamiliar surroundings, providing calves with unfamiliar feed, and castration.

More particularly, the novel cattle management program commences weaning at approximately 50 to 200 days, and more preferably at approximately 100 to 150 days from birth. Young cattle are kept with their mothers in the pasture and are "creep fed" in the pasture by providing liquid feed in a container designed to preclude access by older animals while allowing younger calves to freely feed on such liquid feed supplement. Young cattle are then moved from the pasture to a feedlot for weaning purposes. Prior to or at about the time of weaning, vaccines and a specially formulated liquid feed supplement are administered to the calves for preventing, for example, stress induced sickness due to early weaning. The calves are weaned at approximately 100 to 200 days from birth and provided the same liquid feed supplement used in the pasture feeding, together with conventional feed sprayed with such liquid feed supplement. In one embodiment of the invention, the young cattle are moved to a feedlot which has a feeding container therein having the identical liquid feed supplement fed to such cattle prior to weaning. The feedlot is also supplied with a feed container that has conventional feed therein, such feed coated and/or mixed with the same liquid feed supplement. In this way, young cattle are moved to a place (e.g., the feedlot) where there are present familiar aspects to the young animals, including the feed container used prior to weaning and the availability of the now familiar liquid feed supplement. The smell and taste of the liquid feed supplement on the more conventional feed encourages the animals to start eating more conventional feed sooner and thus, such animals gain weight more rapidly and are healthier during the weeks after their conveyance to the feedlot. This greatly reduces the stress on such animals and, importantly, maintains the eating habits of the animals during such transition.

When the bulls are between approximately seven months and ten months of age, they are castrated using the ligation method and apparatus of the present invention, which is substantially less stressful and more effective than other castration methods. Castration at such time achieves the increased muscle and frame development possible with an intact bull while avoiding the unfavorable characteristics of a mature bull. Also, concurrent with such castration, infection preventative measures are administered, such as a tetanus injection. The present invention provides for a more humane method by which to castrate animals. The bloodless castration device provided by the present invention is a vast improvement over the traditional method of castration involving severing an animal's testicles with a knife during the branding of young calves. The present method is also safer than conventional methods of castration since it does not involve sharp knives typically used in conventional castration procedures where the inevitable movement of an animal during the procedure creates an opportunity for the human operator to suffer cuts to his/her own body.

It is a common experience using conventional practices for young calves, after being removed to a feedlot, to cry out for their mothers and to constantly walk around the feedlot in a semi-panicked and stressed state. During this stressful time period, calves often experience no gain in weight due to their unfamiliarity with the surroundings and their reluctance to eat conventional feed. The stressful conditions and the reduction in the amount of food consumed by such animals, often results in such animals getting sick. Using the present invention, however, it has been found that young calves gain substantially more weight for the first three weeks in the feedlot.

Thus, it is an important aspect of this cattle management program that cattle, and in particular bulls, increase in size and muscle substantially faster than cattle do using conventional cattle raising practices. In particular, by castrating in the age range mentioned hereinabove (rather than the conventional practice of castration at branding time (e.g., birth to approximately two months)), the natural growth hormones secreted by the testicles (namely, testosterone) cause the male animals to grow larger, more rapidly and without the need for (and related expense of) artificial hormones. Further, by castrating during the above-mentioned age range, substantial growth can take place without undesired masculization. Accordingly, the meat derived from such steers has a higher lean-to-fat ratio, with improved cutability characteristics. Tenderness and palatability improvements of meat derived from such animals is also achieved, such factors largely relating to the age of the animal. Accordingly, due to the accelerated growth of cattle raised using this novel cattle management program, cattle may be slaughtered at one year to fourteen months from the date of birth, rather than the more conventional time periods of at least eighteen months to two years from birth. Accordingly, using the present invention, there is a substantial savings in the cattle raising overhead due to the shortened time frame involved. For example, maintenance costs involved in keeping an animal alive for additional months are eliminated, allowing ranchers to not only improve their profit margins, but also to more quickly pay back loans typically required in ranching operations.

Additionally, in a preferred embodiment of the novel cattle management program of the present invention, the liquid feed supplement provided to the cattle has approximately the following ingredients: corn condensed distillers solubles (a by-product of alcohol production); corn steep liquor (a by-product of starch production); vegetable fat (a by-product of corn oil refining) and Protoferm (a by-product of monosodium glutamate). Preferably, the liquid feed supplement comprises approximately 16% protein, of which approximately 56% is natural, with the remaining being non-protein nitrogen in the form of ammonium chloride. The mixture also preferably has approximately 10% fat content and 45% solids. A preferred feed formulation is MIX 30™, available from Timberlake Sales, P. O. Box 7510, Springfield, Ill.

The present inventor is believed to be the first to recognize the advantages of using substantially the same liquid feed enjoyed by calves in the pasture as a feed supplement mixed with more conventional feed mixtures to familiarize cattle with conventional feed. In combination with the novel castration method developed by the present inventor, it is now possible to raise cattle in a manner that significantly increases their growth, reduces stress and provides for healthier weight-gaining animals in a far shorter time period when compared with conventional cattle raising practices. The result is an improved quantity of quality meat yield from such animals and an overall reduction in the costs involved in the cattle raising process.

Other features and benefits of the present invention will become apparent from the detailed description with the accompanying figures contained herein.

BRIEF DESCRIPTION OF THE DRAWINGS

FIG. 2 is a side view, partially cut away, of the apparatus of FIG. 1.

FIG. 3 is a side elevational view of the apparatus of FIG. 1 with the crimping arm in a deflected position.

FIG. 6 is a side view, partially cut away, of an apparatus constructed in accordance with the present invention showing a cutting assembly.

FIG. 7 is a front view of the apparatus of FIG. 6.

DETAILED DESCRIPTION OF THE INVENTION

I. Ligation Method and Apparatus

Figure 1:
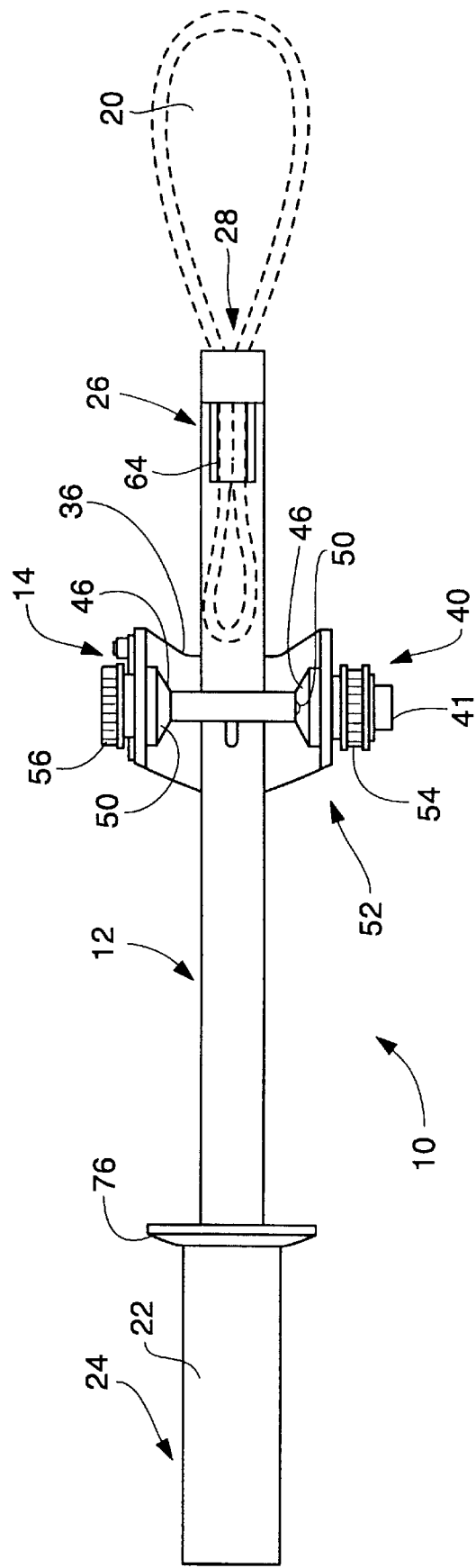
FIG. 1 is a top view of an apparatus constructed in accordance with the present invention.
Figure 4:
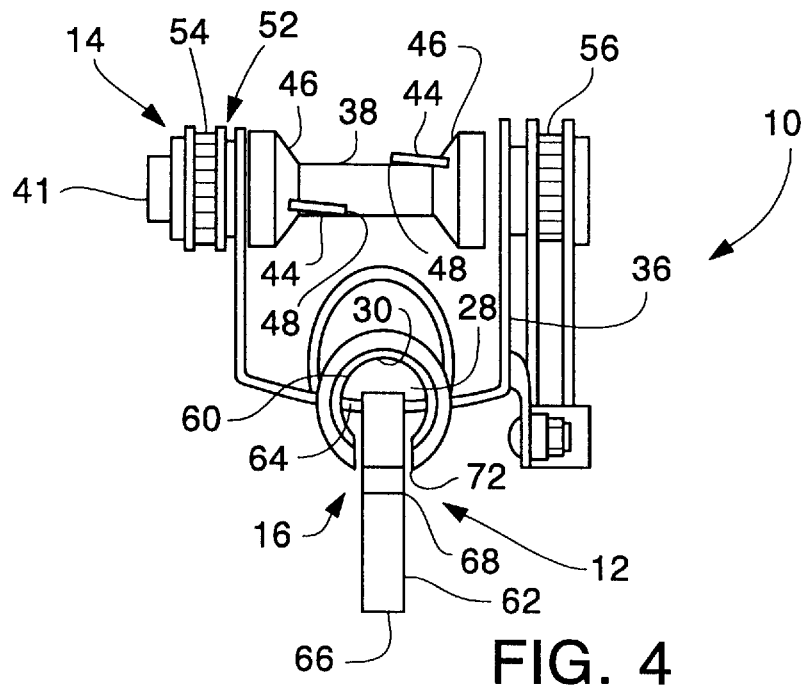
FIG. 4 is a front elevational view of the apparatus of FIG. 1.

Referring to FIGS. 1–4, an apparatus constructed in accordance with an embodiment of the present invention is generally identified by the reference numeral 10. As shown, the apparatus 10 comprises a tool body 12, a winding assembly 14 and a crimping assembly 16.

The body 12 receives a band 18 of ligature material, wherein a loop 20 of ligature material is formed external to the apparatus 10 about an animal body part to be removed. The loop 20 is then progressively tightened by winding the band 18 about winding assembly 14 to substantially cut off blood flow and systemic support to the animal body part. Preferably, the ligature material comprises an elastomeric material such as surgical tubing. However, because of the large tightening forces which can be achieved with the apparatus 10, relatively inelastic band materials such as rope and/or wire may be successfully employed.

The tool body 12, which may comprise steel or other material having sufficient strength to withstand the forces encountered during ligation procedures, has a handle 22 at a first end portion 24 thereof and a second end portion 26 which is adapted to receive the band 18 of ligature material. The handle 22 may be contoured for optimal handling by the user. In the illustrated embodiment, the second end portion 26 includes a passageway 28 sufficient to allow passage of the band 18 therethrough. The second end portion 26 can also include a receptacle 30 adapted to hold a grommet 32 which can be crimped, as will be described below, to secure the band 18 after the loop 20 has been tightened. It will be appreciated that the band 18 of ligature material is pulled rearwardly through the passageway 28 towards the winding assembly 14 as the loop 20 is tightened. As illustrated, the second end portion 26 may be angled relative to a longitudinal portion 34 of the body 12, the angle preferably selected such that a longitudinal direction of the second end portion 26 is directed towards the winding assembly 14, thereby reducing frictional and binding contact between the band 18 and the second end portion 26 as the band 18 is pulled therethrough. Reducing such frictional and binding contact facilitates winding of the band 18 by reducing the effort which must be exerted by the user in winding and reducing the likelihood that the band 18 will become snagged and possibly break.

The winding assembly 14 is attached to the body 12 by way of frame 36 which may comprise steel or other material of suitable strength. Frame 36 provides a distance x between the body 12 and the winding assembly 14 which is sufficient to substantially prevent mechanical interference between the band 18 and the body 12 as the band 18 is wound about the assembly 14. Preferably, the distance x is between about ¼ inch and two inches depending, for example, on the thickness of the band 18 employed. In the illustrated embodiment, the distance x is about ½ inch which has been found to provide sufficient clearance for a broad range of materials, including standard surgical tubings.

In one embodiment of the present invention, the winding assembly 14 comprises a spool 38 which is rotatably mounted on the frame 36 and a winding engagement site 41 operatively connected to the spool 38 is provided which can be rotated by a pneumatic, electrical, or more preferably hydraulic power motor 43, such motor being integral to or alternatively separate from the frame 36. The power tool 45 or motor 43 utilized must be capable of engaging the winding engagement site 41 in a manner so that the winding means 14 is turned or rotated, thus facilitating the accumulation of ligature material on the winding assembly 14. In one embodiment, the winding engagement site 41 comprises a suitably designed protuberance, such as a nut having several sides, or an indentation, similarly having a plurality of sides, engageable by a suitably complementary power tool 45 device that is capable of activating the winding means 14 to achieve rotation thereof. The compatible multi-sided protuberance or multi-sided indentation is configured so that engagement of the power tool 45 or motor device 43 with such protuberance or indentation will facilitate the powered rotation of the winding means 14.

In another embodiment, the powered winding of ligature material is achieved by the incorporation of a pneumatic or electrical device into the tool's 10 overall design so that a separate power tool 45 need not be interconnected or engaged with a separate powered tool. As such, the incorporation of a pneumatic or electrical powered motor 43 that is integral with the castration tool 10 is within the scope of the present invention. An illustrative embodiment of such embodiment is shown in FIGS. 8 and 9.

Figure 8:
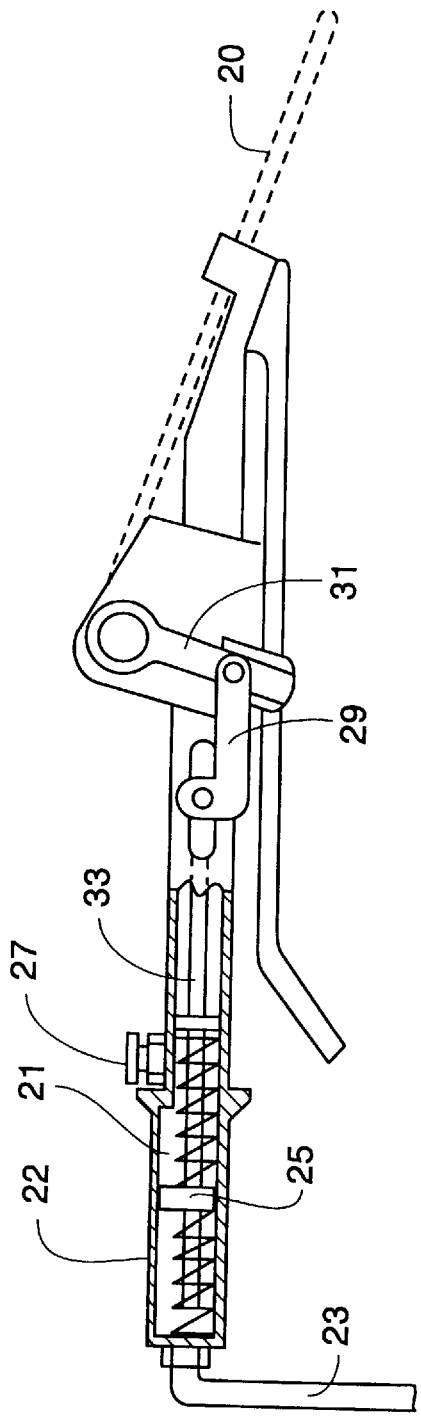
FIG. 8 is a side partial section elevational view of one embodiment of the present invention in which a power winding source is integral with the ligation tool itself.
Figure 9:
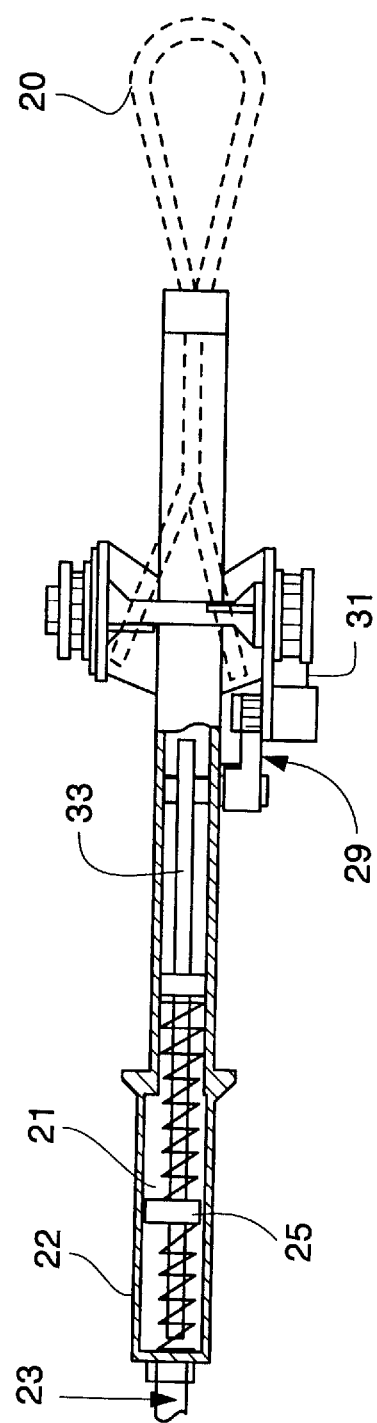
FIG. 9 is a top partial section view of one embodiment of the present invention in which a power winding source is integral with the ligation tool itself.

With reference to FIGS. 8 and 9, a pneumatic device 21 is incorporated into the handle 22 of the tool 10. An air supply 23 can be interconnected with one end of the handle 22 to operate an air piston 25 residing within the handle 22. An air control valve 27 located on the handle 22 can be used to control the winding operation so as to achieve desired winding of ligature material about the spool 38. In one embodiment, a drive linkage 29 between the pneumatic device 21 and the winding assembly 14 is provided to permit operation of a ratcheted lever 31 having an axis of rotation coincident with the axis of rotation of the spool 38. The lever 31 is attached to a ratchet mechanism 52 so that the spool 38 can be selectively rotated in alternative directions. The drive linkage 29 is operatively attached to a piston rod 33 which is driven by the air piston 25 located in the tool's handle 22. Upon operation of the air piston 25, the piston rod 33 is moved back and forth within the body 12 of the device. Through such movement the drive linkage 29 communicates with the ratcheted lever 31 to rotate the spool 38 in a desired direction. Winding of the ligature material 20 around the spool 38 can thus be accomplished by regulating the number of times the air piston 25 is forced forward and backwards, thereby ratcheting the ligature material 20 around the spool 38 to achieve a desired tension of the ligature loop 20. In another embodiment, an electric or pneumatic motor is incorporated into the handle 22 of the tool 10 and is interconnected to a worm gear or other type of gearing mechanism. The worm gear is then operatively positioned to another gear interconnected to the winding spool 38. As can be appreciated by one skilled in the art, numerous types of gearing configurations may be implemented to transfer power from the motor to the winding spool 38.

In some applications, it is important to regulate the tightness or tension of a ligature loop 20 to prevent breakage thereof or to prevent injury to the animal. The tightness of ligature material can be regulated by adjusting the amount of force communicated by the rotation of the winding means 14 by a motor 43. This can be accomplished by, for example, a clutch mechanism 47 either incorporated into the winding means 14 or, alternatively, can be a feature of the power tool 45. For instance, a pneumatic power tool 45 capable of rotating the winding means 14 can be adjusted so that no further rotations occur after a predetermined tension or torque is achieved, at which point air is bled from the pneumatic power tool 45 rather than being used to rotate the winding assembly 14. The ligature material is therefore wound about the winding means 14 to a predetermined tension, such tension regulated by a clutch mechanism 47 operatively associated with the motor 43 or in alternative embodiments, a feature of the power tool 45.

As can be readily appreciated, the rate at which the loop 20 is tightened will depend upon the diameter of the spool 38 and the speed of rotation of the spool 38. In addition, the tension which can be imparted to the band 18 by winding the band a predetermined number of times around the spool 38 or, alternatively, by gauging the tension or torque exerted on the winding assembly 14 so that at a predetermined desired tension, the spool 38 is no longer rotated. The diameter of the spool 38 can therefore be selected to allow the desired rate and degree of tightening. Although it is believed that a broad range of spool 38 diameters would provide adequate results, the illustrated spool 38 has a diameter between about ½ inch and ¾ inch. Such a diameter allows for rapid tightening of the loop 20 and allows the loop 20 to be sufficiently tightened to substantially cut off blood flow and systemic support to the body part to be removed.

The spool 38 further includes fasteners 44 to attach the band 18 to the spool 38. The fasteners 44 may comprise a slotted portion of the spool 38, a clip biased against the spool 38 or any other device by which the band 18 can be secured to the spool 38. Where an elastomeric band is employed, is it expedient to provide a fixed element closely adjacent to a surface of the spool 38 so that the band 18 can be frictionally secured therebetween. In the illustrated embodiment, the fasteners 44 comprise cantilevered rods extending inwardly from flanged end portions 46 of the spool 38. The fasteners 44 can be positioned such that the space between the spool 38 and a fastener 44 is progressively restricted from a free end 48 to a base 50 of the fastener 44. Such a configuration allows the band 18 to be quickly and reversibly secured to the spool 38 by inserting the band 18 between the spool 38 and the free end 48 and then sliding the band 18 towards the base 50 until the band 18 is securely wedged therein.

The winding engagement site 41 is interconnected to the spool 38 such that the spool 38 can be rotated by turning of the winding means 14. A ratchet assembly 52 can be employed to facilitate rapid tightening of the loop 20. The assembly 52 comprises a first ratchet and pawl mechanism 54 which cooperates with a second ratchet and pawl mechanism 56 at the opposite end of the spool 38 to allow rotation of the spool 38 in only one direction. The user can thus tighten the loop 20 through repeated turnings of the spool 38 and the pneumatic or electric winding device 43 can be adjusted so that at a desired tension, no further winding of the spool 38 occurs. The present invention therefore provides a method and device that facilitates the speedy ligation of animal parts, and thus considerably shortens the time period required to perform the ligation procedure. This spares the user from exposing himself/herself to extended periods of danger encountered when working with large animals and lessens the discomfort of the animals.

Although particular dimensions for the illustrated embodiment have been provided, it is within the scope of the present invention to have a tool body of any dimensions, thus allowing for variation of the distance between the operator and animal.

Although not shown, it will be appreciated that the ratchet assembly 52 could be eliminated and the winding engagement site 41 could instead be rigidly interconnected to the spool 38 with appropriate modification of the apparatus 10. It will be further appreciated that a winding engagement site 41 can be positioned on either or both sides of the body 12 to facilitate right hand or left hand users.

After the loop 20 has been tightened, the loop size can be maintained by securely interconnecting portions of the band 18 adjacent the loop 20. The portions may be interconnected by using an adhesive; stapling, pinning or heat sealing the band 18; binding portions of the band with wire, rope or the like; or any other suitable method for securing the loop 20.

In the illustrated embodiment, a crimping assembly 16 is provided to crimp a grommet 32 after the loop 20 has been tightened, thereby securing the loop 20. The grommet 32 preferably comprises a cylindrical structure having an interior passageway sufficient to allow passage of the band 18 therethrough and can be formed from aluminum or other deformable material. During the ligation procedure, the grommet 32 is housed within a receptacle 30 of the second end portion 26. As shown most clearly in FIG. 4, the receptacle 30 can include an internal annular shoulder 60 such that the grommet 32 can be positioned by sliding the grommet 32 into the receptacle 30 until an end of the grommet 32 abuts the shoulder 60.

The grommet 32 used with the present invention can be of any desired shape and dimension to fit appropriately in the receptacle 30. The grommet 32 must be capable of being properly crimped in a manner sufficient to hold two bands 82 together so as to form a loop 20 of ligature material. The grommet 32 must retain the loop 20 in a tensive condition during the atrophy process which may take several weeks. Further, the grommet 32 is designed so as to securely fasten the ligature material without significantly damaging the material. The grommet 32 can be a completely enclosing angular structure or may alternatively be configured with side portions bendable to secure each individual end of the ligature material, thus independently fastening each end without being dependent upon the adjacency of the other end to achieve a secure loop 20. The grommet 32 may further include indexing means comprising indentations or protuberances so that the grommet 32 is properly oriented within the tool 10 to achieve a desired crimping configuration.

Figure 5:
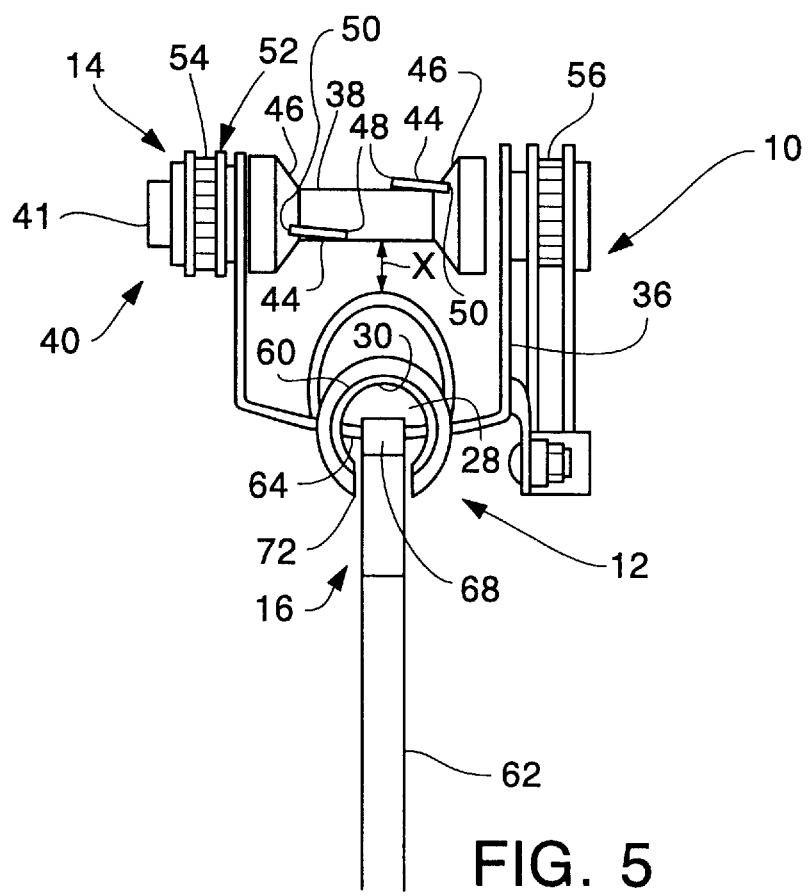
FIG. 5 is a front elevational view of the apparatus of FIG. 1 with the crimping arm in a deflected position.

The crimping assembly 16 comprises a lever 62 which is pivotally mounted on the body 12 by way of a fulcrum 64 such as a pin. The user can move the lever 62 from a retracted position (FIG. 3) to an extended position (FIGS. 4 and 5) by urging the rearward end 66 of the lever 62 downwardly as viewed in the figures. In the extended position, the forward end 68 of the lever 62 extends into the receptacle 30 to deform the grommet 32. As shown, the fulcrum 64 is preferably positioned towards the forward end 68 of the lever 62 so that a relatively small downward force exerted on the rearward end 66 of the lever 62 by the user results in a greater crimping force on the grommet 32.

The fulcrum 64 penetrates a bulge portion 70 of the lever 62 which extends through a slot 72 in the body 12. Forwardly from the fulcrum 64, the lever 62 tapers so that the lever 62 can be fully withdrawn from the receptacle 30 in the retracted position. In addition, the illustrated lever 62 includes a downwardly extending portion 74 adjacent the rearward end 66 of the lever 62 to avoid mechanical interference with a flange 76 of the handle 22 and to provide sufficient clearance between the body 12 and the lever 62 for gripping by the user. If desired, the lever 62 may be contoured for optimal handling by the user or a grip (not shown) may be interconnected with the lever 62 for this purpose.

Referring to FIGS. 6 and 7, side and front views, respectively, of an apparatus 78 constructed in accordance with the present invention are shown. The apparatus 78 includes a cutting assembly 80 for cutting the band 82 rearwardly of the grommet 84 after the loop 20 has been tightened. Any device for cutting the band 82 may be employed in accordance with the present invention. For example, a hand-held razor, scissors or other cutting tool 10 may be employed. In the illustrated embodiment, the assembly 80 comprises a razor 88 slidably mounted within a housing 90 which is interconnected to or integral with the apparatus body or frame. Preferably, the cutting assembly 80 severs the band 82 a suitable distance rearwardly of the grommet 84 to reduce the likelihood that the band 82 will be pulled through the grommet 84 after severing. In this regard, it will be appreciated that elastomeric bands tend to constrict under tension and expand after severing such that such bands may slide a distance through the grommet 84 before becoming secured therein.

The razor is slidable from a retracted position, wherein the cutting surface of the razor 88 is protectively housed within housing 90, to an extended position (as shown in phantom in FIG. 7) wherein the cutting surface of the razor 88 extends into the band passageway to cut the band 82. The razor 88 can be moved from the retracted position to the extended position by pressing downwardly on an upper surface 92 of the razor 88, such that the upper surface 92 is urged downwardly through finger cut-out 94. Preferably, the razor 88 is biased upwardly, e.g. by a spring, so that the razor 88 remains in the retracted position until the razor 88 is pressed downwardly. Alternatively, a cutting mechanism 88 can be pivotally connected to the tool body 10 so that the band 82 is severed from below by simply pivoting of the cutting mechanism to bring the razor 88 into contact with the band 82. It will be appreciated that such a pivoting cutting mechanism can be used in embodiments where continuous or long lengths of banding is utilized and is not confined to use with continuous loops.

In operation, a tool 10 may be employed in accordance with the present invention to ligate a body part as follows. Initially, a band of ligature material is either looped around the body part and inserted through an end portion of the tool 10 and a grommet 32 housed therein, or a loop 20 is preformed and then positioned around the body part to be ligated. End portions of the band can then be attached to a spool by sliding the end portions between fasteners and the spool such that the end portions are frictionally engaged therebetween. Although not shown in the illustrated embodiments above, it will be appreciated that it would be sufficient to attach only one end portion of the band to the spool. For example, one end portion of the band could be connected to the spool and a second end portion could be connected to the body. In this regard, attaching the band to the spool at two end portions has the advantage that the band can be tightened quickly and evenly. However, attaching the band to the spool at only one end portion and allowing the other end portion to remain stationary as the band is tightened has the advantage that the stationary end portion need not be severed from a supply of band material prior to winding the band.

After the band is secured to the spool, the band can be tightened by turning or rotating the winding means 14. The band can be tightened by operation of a pneumatic or electrical winding tool 10 that engages the winding assembly 14 to thereby cause the spool to rotate, tightening the ligature loop 20. The present invention therefore provides a method and device for tightening a loop 20 around a body part without expenditure of physical strength, such as a user's hand strength. The tightness of the loop 20 is therefore not limited by the user's hand strength, allowing for the expedited ligation of body parts.

When the loop 20 is tightened sufficiently, the loop 20 can be secured by moving a crimping lever to an extended position thereby deforming the grommet 32 so that the band portions therein are frictionally secured. Thereafter, the band may be severed with a cutting tool 10, e.g., a razor, rearwardly of the grommet 32 leaving the loop 20 attached to the body part.

Another aspect of the present invention involves an endless elastomeric ligature loop 100 used for ligation of body parts, and particularly for castration. The prior art discloses the manual formation of an endless loop around a body part of an animal utilizing two ends from a substantially linear band of ligature material. The ends of the ligature bands are then attached to a means for pulling one or both of the ends of the ligation material to tighten the manually formed loop around the body part. In contrast, the present invention provides a preformed endless loop that is easy to attach to a tool for winding or pulling, and subsequently decreases material costs due to the absence of any excess length of ligature material used in securing such material to the ligation tool. The use of preformed endless loops of material, particularly loops having a pre-attached grommet thereon, reduces the time required to apply the endless ligature loop around the body part of a restrained animal. In a preferred embodiment, the endless loop is manufactured from an elastomeric material having a high tensile strength that is resistant to abrasion and tearing. More preferably, the elastomeric material is comprised of a non-hollow rubber material either molded or extruded to produce a finished elastomeric product without ends. As an alternative to using a manufactured preformed elastomeric loop without ends, an elastomeric endless loop may be formed by attaching or connecting the two ends of a straight length of an elastomeric band of rubber or surgical tubing with a clip, wire band, grommet, or other device which prevents the two ends from being separated. In a preferred embodiment, a heavy gauged wire may be used to secure the two ends of the elastomeric band and may further include an end piece capable of being attached to a means for winding or pulling (e.g., hook-like structure).

Figure 12:
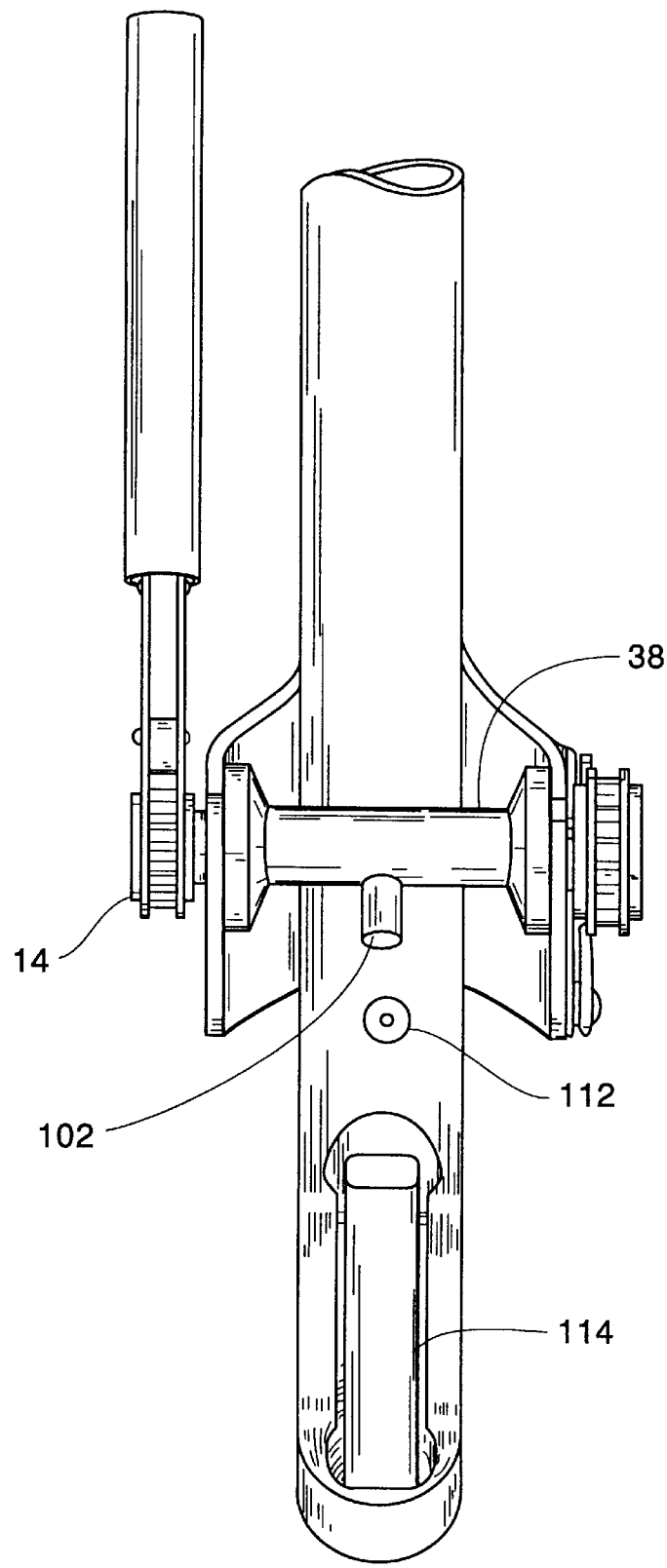
FIG. 12 is a perspective view of the tool showing an integral prong attached to the winding spool.

The endless elastomeric ligature loop 100 is positioned in the receiving end of the tool and connected to an attachment means located on the winding spool 38 (or any suitable pulling means). In a preferred embodiment, a hook-like structure or prong is used to contact the loop and allow the loop to be pulled or wound as shown in FIG. 12. The prong 102 attached to the winding spool 38 may have an integral hook or other type of attachment mechanism to prevent loss of contact with the endless loop during a winding or pulling operation. In a preferred embodiment shown in FIGS. 10 and 12, a hook 104, which attaches to the endless loop is connected to a winding tether 106, which is in turn connected to the winding spool 38. As the winding spool 38 is rotated, the winding tether wraps around the winding spool and begins pulling the endless loop 100 towards the winding spool 38 once sufficient slack is removed from the winding tether 106. The winding tether 106 may be comprised of rope, leather, steel cable, or any other suitable material with a tensile strength sufficient to withstand the forces necessary to operatively tighten the elastomeric loop around the scrotum or other body part of an animal. The endless loop 100 can thus be attached to the winding mechanism quickly without being torn or damaged when tension is placed on the endless loop 100. Furthermore, by utilizing an endless loop in combination with a winding tether 106, significant savings in material costs are realized since the overall length of the endless loop can be decreased. The winding tether 106 and integral hook assembly may be seen in FIG. 10.

Once the endless loop 100 is pulled and/or wound to a desired tension, the loop is constricted so that it is secured around the body part to be ligated. Any suitable means of securing two opposing portions of a loop can be used, including mechanically affixing the loop together or thermally melting the loop material to form a bonding point. Preferably, a grommet 32 is used to secure the endless loop material in a fixed position once sufficient tension is placed on the endless loop to apply adequate pressure around the body part of an animal. The grommet 32 is comprised of metal or any other material which can be permanently deformed. The material preferably has a surface smooth enough to prevent any abrasion when in contact with the elastomeric ligature material, thus preventing tearing of the ligature material. More preferably, the grommet is comprised of rolled flat wire with a length and width sufficient to prevent the ligature material from slipping through the grommet 32 after the grommet 32 is deformed upon the endless loop 100.

Figure 13:
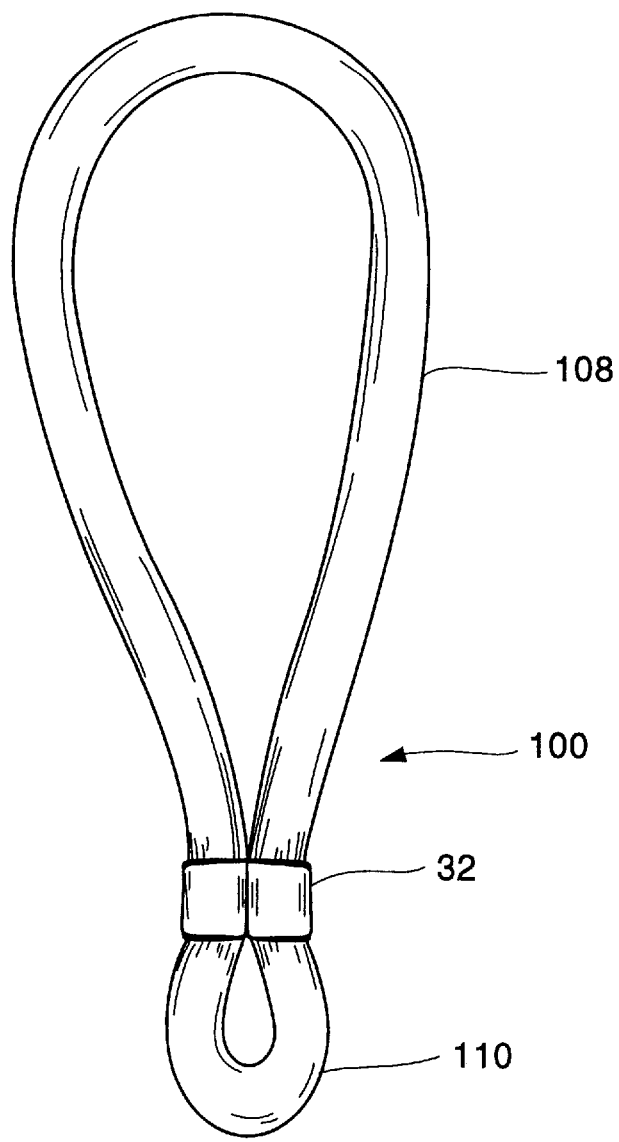
FIG. 13 is a plan view of the endless elastomeric loop and attached grommet.

In one embodiment, a grommet 32 is attached to the endless loop 100 prior to actual use, thus assuring that the grommet 32 is attached in a proper manner not likely to damage the endless loop and also preventing the possibility of tightening the loop without first having a grommet in place. Furthermore, by preattaching the grommet 32 to the endless loop, time is saved in the ligation process since the step of feeding the ligature material through the grommet 32 is eliminated. Preferably, and as depicted in FIG. 13, the grommet 32 is attached to the endless loop 100 between a forward end and rearward end of the endless loop, thus forming a forward loop 108 and rearward loop 110, similar to a modified figure-eight or hour-glass configuration. The forward loop 108 extends forward of the receiving end of the tool and the rearward loop 110 extends rearward of the receiving end of the tool. More preferably, the forward loop 108 should be of sufficient circumference to allow it to be easily placed around a selected body part of an animal, such as a scrotum. The rearward loop 110 preferably has a circumference large enough to either allow the attachment of a hook attached to a winding tether 106 (or other pulling means), or to be placed over a prong 102 extending from the winding spool 38. The pre-attached grommet 32 must be loosely attached to the band in a manner that allows the ligature material to slip through the grommet 32 until desired tension on the body part is achieved. At such time, the grommet 32 is deformed to permanently secure the tightened band around the body part.

The receiving end of the tool may have a variety of geometric configurations suitable to receive an equally numerous number of grommet 32 designs. Preferably, the receiving end of the tool has a receptacle 30 with substantially rigid opposing side walls. More preferably, the opposing side walls and opposing top and bottom walls are parallel to one another, whereby the receptacle is substantially square or rectangular in shape. Other embodiments (not shown) can have a receiving end that is open on a top, bottom or side to facilitate easier loading of grommets into the tool.

Figure 11:
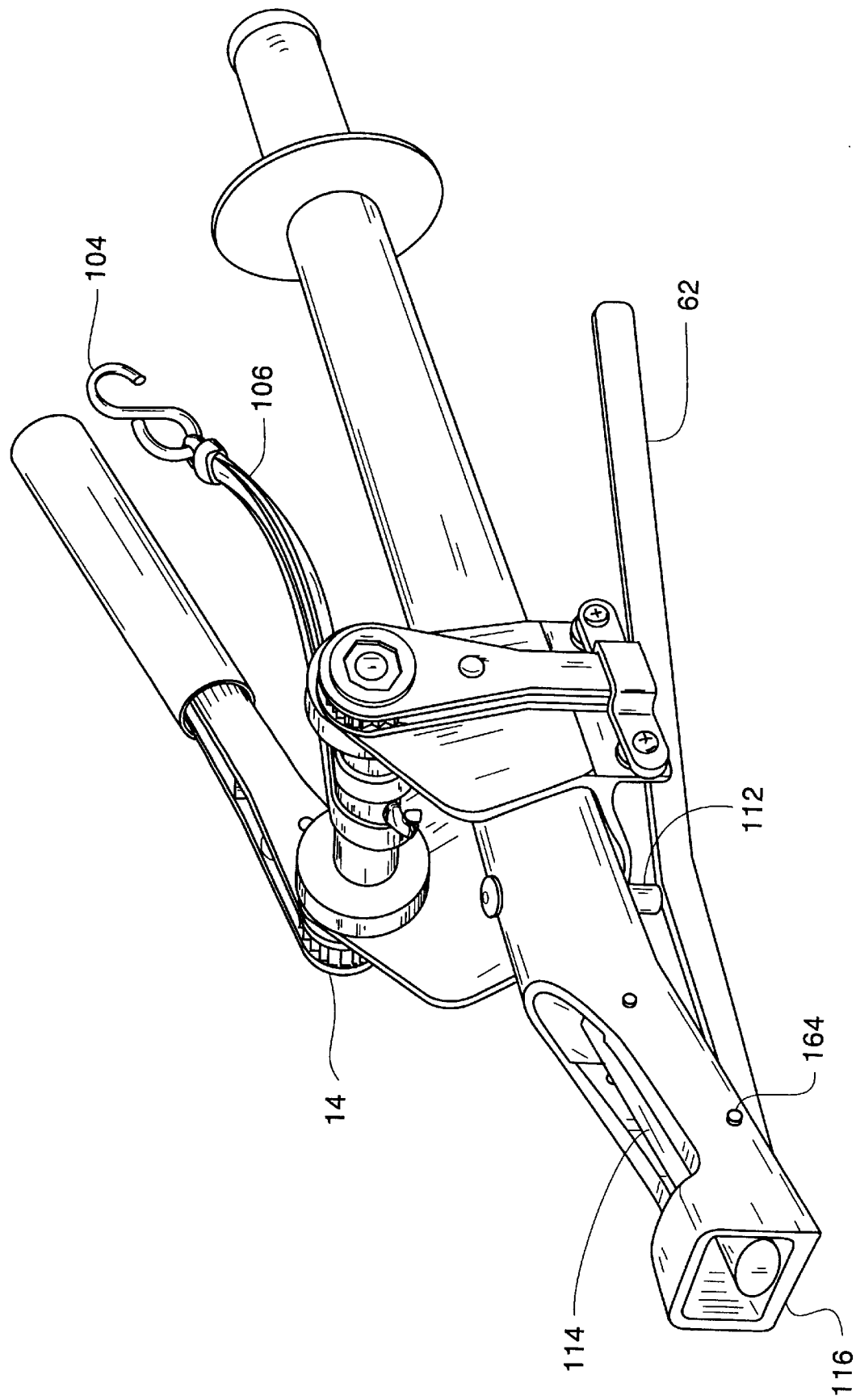
FIG. 11 is a perspective view of the present invention showing the biasing pin, lever, crimping bar and substantially square receptacle located in the receiving end of the tool.

As shown in FIG. 11, the lever 62 pivotally mounted on the body of the tool may be held in a biased position with a biasing pin 112 against the grommet 32 when the grommet is in the receiving end of the tool. The biasing pin 112 may be metallic or any other durable material and extends downward from the tool body. By utilizing a spring, coil or other biasing means, the biasing pin 112 applies constant downward pressure on the lever arm 62, which transfers pressure against the grommet 32 located in the receptacle 30 of the tool. The constant pressure applied by the biasing pin 112 prevents the grommet 32 from inadvertently falling out of or from becoming mispositioned in the receptacle 30 of the tool. Once the endless loop 100 is tightened sufficiently around the body part of the animal, the lever 62 is used to permanently deform the grommet 32 upon the endless loop 100, thus preventing the endless loop 100 from slipping through the grommet. After the grommet 32 is deformed, the lever position is reversed by applying pressure on the rearward portion of the lever in a direction towards the tool body, thus disengaging the tool from the grommet, and thus from the formed endless loop 100. Other means for retaining the grommet in the tool (not shown) include the use of a magnet to reversibly hold a ferrous grommet in place and the use of reversibly flexible structures on the tool and/or the grommet, that act to secure the grommet in a loose fashion to the tool.

Figure 10:
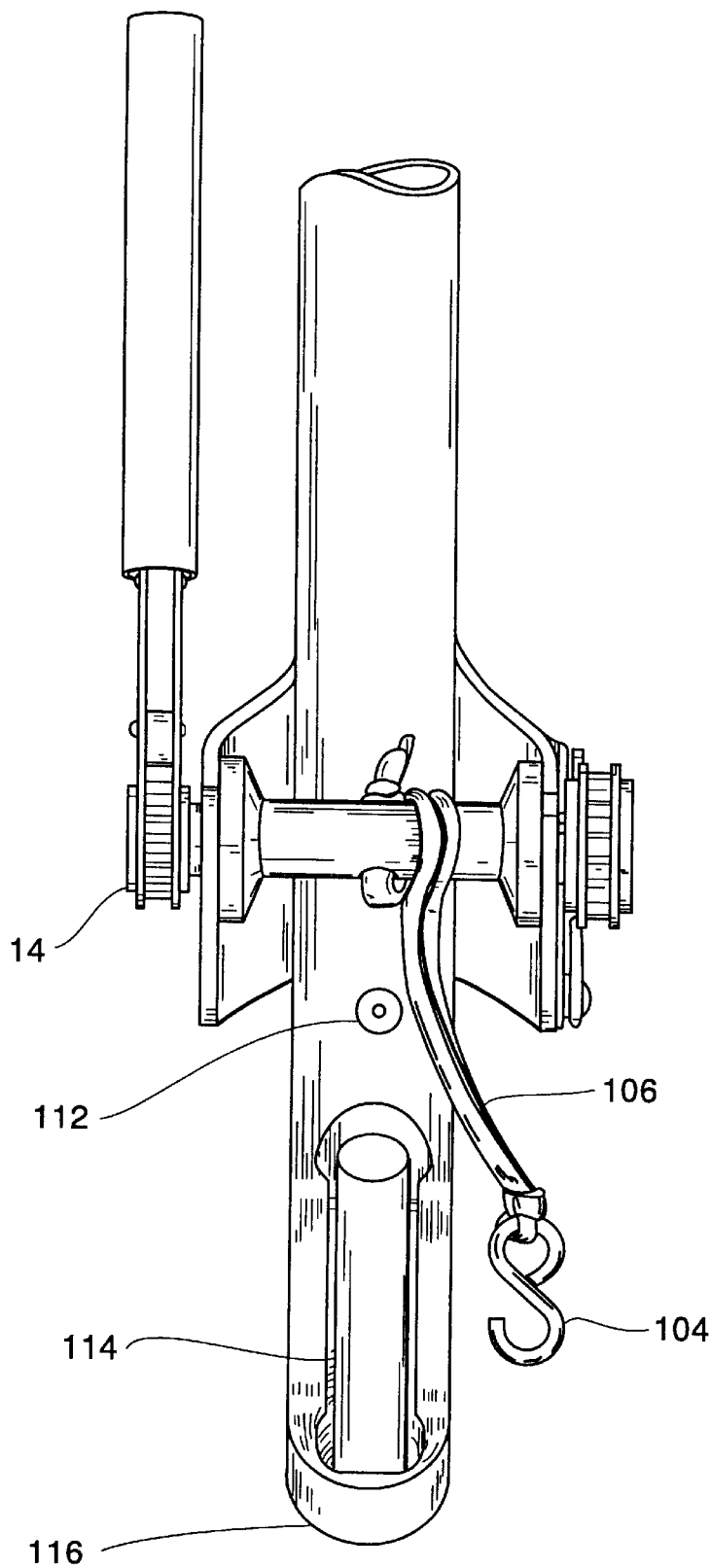
FIG. 10 is a top view of the present invention depicting a winding tether attached to a winding spool and a crimping bar pivotally mounted in the receiving end of the tool.

As illustrated in FIG. 10, the crimping assembly may additionally include a crimping bar 114 located within the receiving end of the tool. Preferably, the crimping bar 114 is pivotally positioned within the receiving end 116 of the tool. The crimping bar 114 is positioned to transfer force from the lever 62 to the grommet 32 when the grommet is positioned in the receptacle 30 in the receiving end 116 of the tool. The crimping bar 114 may be made of steel or other suitable material hard enough to deform the grommet. More preferably, the rearward end of the crimping bar 114 located closest to the winding mechanism of the tool is riveted to the tool body, while the opposite end of the crimping bar 114 is positioned against the grommet 32. As the lever handle is pushed downward and away from the tool body, the upper surface of the lever 62 transfers force to the crimping bar 114, which rotates or pivots upward around the rivet, deforming the grommet. Although the crimping bar 114 used in the present invention has a circular cross-sectional shape, any geometric configuration capable of deforming the grommet may be utilized effectively.

One aspect of the present invention therefore relates to a ligation tool having a pivotally mounted lever 62 that is operated after ligation material is tightened sufficiently around a body part to be ligated, the operation of such lever effective to crimp a grommet 32 to secure the ligation material together. Prior art devices have utilized a crimping structure involving elongate crimping rods that when rotated, pivot crimping dogs against a grommet to crimp the grommet about tensed ligature material. (See Wadsworth, U.S. Pat. No. 4,691,704). The use of the pivotally mounted lever mechanism to crimp a grommet as disclosed herein provides for a far easier method of operation than crimping operations involving prior art devices. (See FIGS. 2, 3, 6 and 11).

The deformation of the grommet against the endless loop 100 thus maintains the endless ligature loop in substantially constant tension around a scrotum or other body part of the animal. Although a grommet is preferably used to secure the endless loop in a fixed position around a body part of an animal, other means for securing the endless loop will be obvious to those skilled in the art. These means include, but are not limited to, the use of plastic or metallic bands or straps, glues, and the application of heat to effectively melt the elastomeric ring in a substantially fixed position.

In a further embodiment of the present invention, means for pulling the endless elastomeric loop 100 rearward to apply tension to the elastomeric loop may be accomplished by rotating the elastomeric loop behind the receiving end of the tool in a direction substantially perpendicular to the longitudinal axis of the tool. This twisting of the loop material around itself (similar to the twisting of a rubber band on a toy propeller airplane) effectively tightens the loop around a body part and eliminates the need for any pulling mechanism. Preferably, the endless elastomeric loop 100 is attached to a sleeve (not shown) which rotates within the tool body and includes an integral hook or pin which attaches to the endless loop. As the sleeve rotates, the endless loop located rearward of the receiving end 116 of the tool rotates, thus shortening the endless loop and applying tension on the portion of the endless loop located forward of the receiving end of the tool. Once sufficient tension is applied to the endless loop 100, a grommet 32 may be attached to the endless loop 100 and deformed at a point adjacent the body part to be ligated.

Another aspect of the present invention involves a method for ligating a body part of an animal, preferably a scrotum. The method involves manually passing a preformed endless loop of ligature material around the body part of the animal. The endless loop is then pulled using various means integral to the ligature tool (e.g. winding mechanisms, pulling mechanisms, etc.) to tighten the loop around the animal's body part. Once the endless loop is sufficiently tightened, the endless loop is secured to maintain adequate pressure around the animal's scrotum. Preferably, the step of securing comprises deforming a grommet around the endless loop, while the pulling of the endless loop is accomplished by winding the endless loop around a winding spool integrally attached to the ligature tool. To improve the efficiency and cost of the method, a winding tether and attached hook may be utilized to reduce the overall length of ligature material necessary. After the grommet is deformed around the endless loop, the excess ligature material not applied around the animal's body part may be removed by cutting the endless loop that is not around the body part with a sharp knife, razor blade or other suitable instrument. Alternatively, the band material can be unwound or otherwise released from the tool, thus eliminating the need to cut the band so as to release it from the tool.

The present invention has a number of advantages over other ligation methods and tools. First, the present invention allows a band to be tightened quickly and easily, thereby reducing the time that the animal must be restrained. In addition, the present invention allows the band to be set tightly such that blood flow and systemic support to the body part can be reliably cut off, thereby reducing the likelihood of swelling, infection, prolonged stress to the animal and/or failure of the ligation procedure. Further, because the band is progressively wound about the spool as the loop 20 is tightened, tension forces are spread relatively evenly over the band during the ligation procedure, thereby reducing the likelihood that the band will fail. It is a further advantage of the present invention that larger and stronger elastomeric materials, or relatively inelastic materials, may be used. The present invention also has ease-of-use advantages as band tightening and crimping can be accomplished with relatively little effort. Additionally, the use of a preformed endless elastomeric loop saves time by eliminating the step of attaching loose ends of an elastomeric band to a means for pulling during the ligation operation. Ligature band material costs are also reduced by utilizing a winding tether which is attached to a pulling means, such as the winding spool of the present invention. Further, by preattaching a grommet to the endless loop, proper positioning of the grommet around the endless loop is assured. The possibility of the grommet being jarred from proper positioning in the receiving end of the tool is also minimized by means for holding the grommet in place, for example, by use of the biasing of the lever and crimping bar as previously discussed.

Figure 16:
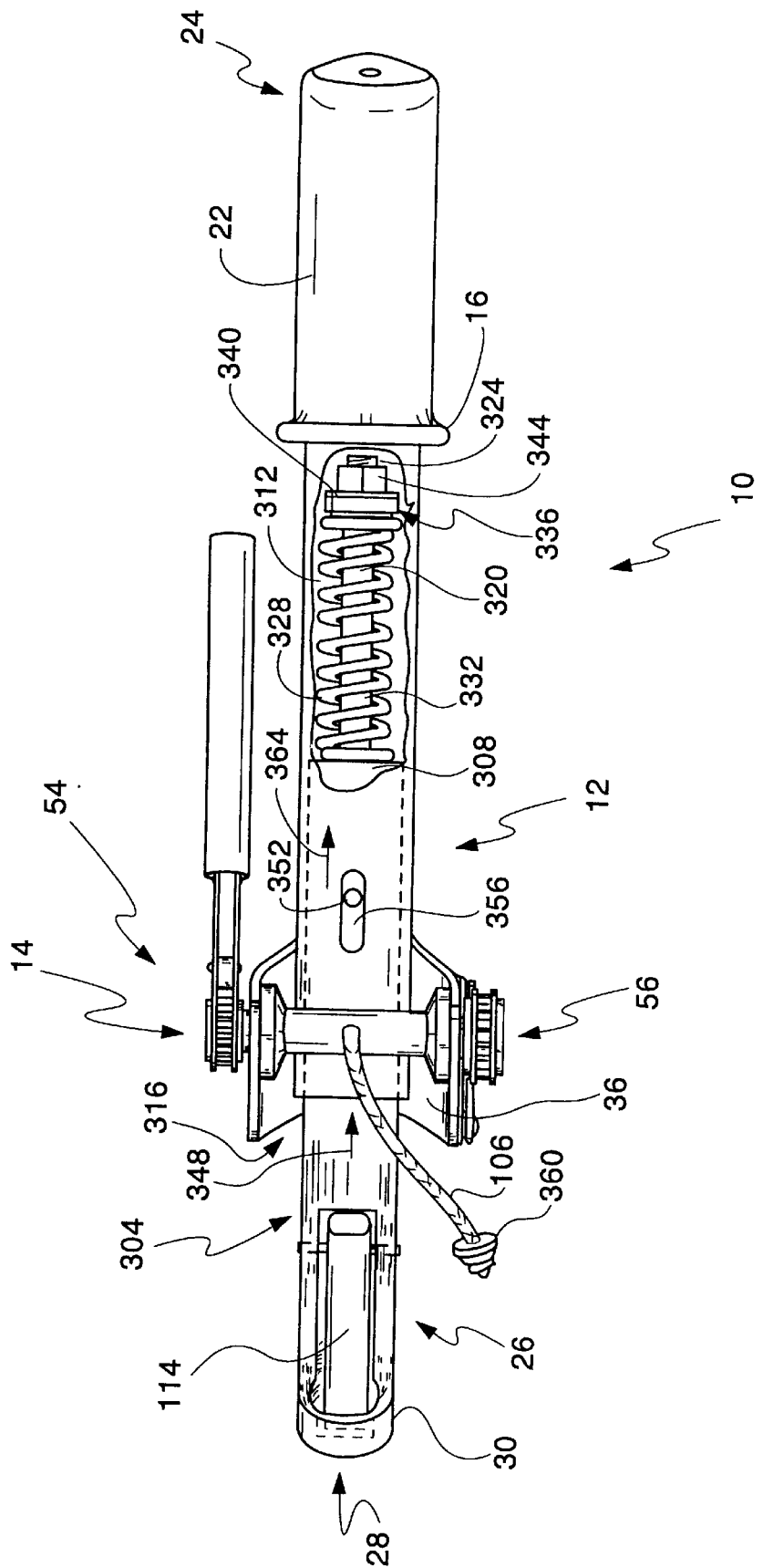
FIG. 16 is a plan view or top view of a ligating tool constructed in accordance with the present invention, wherein this embodiment includes a tension indicator for displaying to an operator of the tool the amount of tension being provided on an elastomeric loop for ligation.

FIGS. 16–19 and 21–23 include further embodiments of the castration apparatus 10 of the present invention. Note that FIG. 16 provides a top view of the castration apparatus 10 that illustrates many of the aspects of the embodiments in FIGS. 16–19 and 21–23. Accordingly, for illustration purposes, a portion of the body 12 is cut away in FIG. 16 to illustrate internal components. Further, the embodiments of these figures are different from previous embodiments in one or more of the following ways:

(a) there is a castration loop tensioning indicator (352) provided on the apparatus 10 (FIG. 16) for assisting in determining when an effective castration tensioning has been applied to a castration loop such as various embodiments of the loop 100 provided hereinabove (e.g., tension of up to about 80 to about 120 lbs, more preferably about 100 lbs);

(b) there are alternative configurations for crimping a grommet 32 (FIGS. 17–19) once an effective castration tension has been placed on a loop 100. In particular, these embodiments are similar to the embodiment of FIG. 11 in that the grommet 32 has its opposing perimeter sides squeezed together between the crimping bar 114 and the receptacle 30 in a manner so that the opposed sides of the perimeter remains substantially parallel thus providing a more secure castration loop locking ability;

(c) there is an alternative configuration for the grommet crimping bar 114 and related components (FIGS. 21–23) so that the action of the lever 62 both crimps a grommet 32 and automatically cuts the excess elastomeric material from the loop after the grommet has been crimped.

Referring now to FIG. 16, this figure illustrates one embodiment of the castration apparatus 10, wherein a tensioning indicator 364 is illustrated. For brevity, components of this embodiment having similar functionality and structure to previous embodiments are labeled identically. Accordingly, only the new or modified features related to the tension indicating capabilities of this embodiment are herein described. Thus, note that the body 12 has been truncated so that it no longer extends to the receptacle 30. Instead, the body 12 (also denoted a body member) truncates approximately at the forward end of the frame 36. For providing the second end portion 26 of the present embodiment, a body member insert (or simply, body member) 304 is provided, wherein the end 308 of the body insert 304 (that is opposite the second end portion 26) is positioned within a longitudinally extending bore 312 of the body member 12, wherein this bore extends from an open end 316 to at least the handle 22. Interior to the bore 312 and extending rearwardly from the body insert 304 is a reduced diameter shaft 320 having a threaded free end 324. Inserted onto the shaft 320 is a compression spring 328 and a spring aligning spacer 332, wherein the spacer 332 is of sufficient length along the shaft 320 so that the central axis running the length of the compression spring 328 is substantially coincident with the length of the shaft 320. Additionally, also provided about the shaft 320 and adjacent to the compression spring 328 are one or more washers 336 that provide a seat for the adjacent end of the compression spring 328 when the spring is being compressed as described hereinbelow. On the opposite side from the spring 328, the washers 336 abut against a retaining member 340 that is fixed to the interior of the longitudinally extending bore 312 of the body 12, and that has a central opening of sufficient diameter to allow the threaded free end 324 to pass therethrough and yet effectively retain the washers 336 on the side of the retaining member 340 opposite the handle 22. Additionally, on the side of the retaining member 340 having the handle 22, there is a bolt and washer assembly 344 secured to the threaded free end 324 of the shaft 320. Accordingly, given that the compression spring 328, when not under compression, is slightly longer than the distance between the end of body insert 308 and the washers 336, the assembled configuration as shown in FIG. 16 firmly secures the body insert 304 into the body 12 in a manner that allows the body insert 304 to compress within the longitudinally extending bore 312 when an effective amount of force is provided on the body insert 304 in the direction of arrow 348.

Attached to the body insert 304 toward the end 308 is the tension indicator 352. In the present embodiment, the tension indicator 352 is viewable by a user of the apparatus 10 through a window or cut-out 356 in the body 12. Note that the tension indicator 352 can project outwardly from the body insert 304 and into the window or cut-out 356 so that this indicator remains aligned within the window or cut-out 356, and additionally assists in securing the body insert 304 within the body 12.

In operation of the present embodiment of the apparatus 10, when an elastomeric loop such as loop 20 and/or loop 100 described hereinabove, is provided with a grommet 32 and inserted into the receptacle 30 with a portion of the loop extending beyond the receptacle 30 and surrounds a body part to be ligated, then a user operates the present embodiment of the invention substantially as before. That is, referring to a loop 100 as shown in either FIGS. 13 or 14 as examples, once the loop is positioned so that the grommet 32 is within the receptacle 30, the knob 360, that is threaded onto the winding tether 306, is inserted into the rearward loop 110 and the user operates the apparatus 10 substantially as described hereinabove. However, during the winding of the tether 106 and the rearward loop 110 about the winding assembly 14, a compression force on the spring 328 in the direction of arrow 348 progressively increases throughout the winding process. Accordingly, the tension indicator 352 moves within the window or cut-out 356 in the direction of arrow 364. Thus, once the tension indicator 352 has moved a measured amount in the direction of arrow 364, this movement is indicative of a specific amount of ligating tension in the forward loop 108. Therefore, once the user sees that the tension indicator 352 has moved at least the expected distance in the direction of arrow 364, then the lever 62 (e.g., FIG. 11) can be pivotally rotated toward the animal being ligated (as in previous embodiments of the apparatus or tool 10) for crimping the grommet 32, or, more precisely, for pivoting the crimping bar 114 to deform the grommets and thereby tightly secure the size of the forward loop 108 about the body part to be ligated. Note that various techniques can be embodied within the present apparatus 10 for indicating to the user the amount of tension being provided on a loop 100. For example, adjacent the window or cut-out 356 may be markers indicating the pounds of tension being provided on the loop 100. Alternatively, such markers may be provided on the body insert 304.

Note, as an aside, it is believed that approximately a tension within the range of 70 to 150 pounds is sufficient for castration of bulls. More precisely, it is believed that a tension in the range of 90 to 110 pounds is effective for bull castration.

Additionally, embodiments of the apparatus or tool 10 can be provided wherein the winding assembly 14 is power driven and a power cutoff or reducing sensor is positioned so that when a predetermined tension is reached, the sensor is activated for halting the winding assembly 14 from further winding. Accordingly, such a sensor may be activated by a predetermined amount of overlap of the two body members 12 and 304. Further, by, e.g., varying a position of such a sensor (or pieces thereof) along the length of the body members 12 and 304, a different overlap of the body members can be obtained when the winding power is cut off. Thus, by this means, a different desired tension setting for ligation can be easily provided by the present invention. Moreover, in one preferred embodiment of the tool 10, wherein the winding assembly is powered hydraulically, a relatively simple valve is provided to regulate the ligation tension, as one skilled in the art will understand.

Additionally, as one skilled in the art will also understand, a functionally similar mechanical sensor can be provided that mechanically links the winding assembly 14 so that at a predetermined tension, the ratchet and pawl mechanism 54 fails to turn the winding spool 38. Accordingly, by incorporating such a sensor into, e.g., a pneumatically driven embodiment, the tool 10 can be operated by a single manual trigger for applying pneumatic pressure until the spool ceases to wind.

Figure 17:
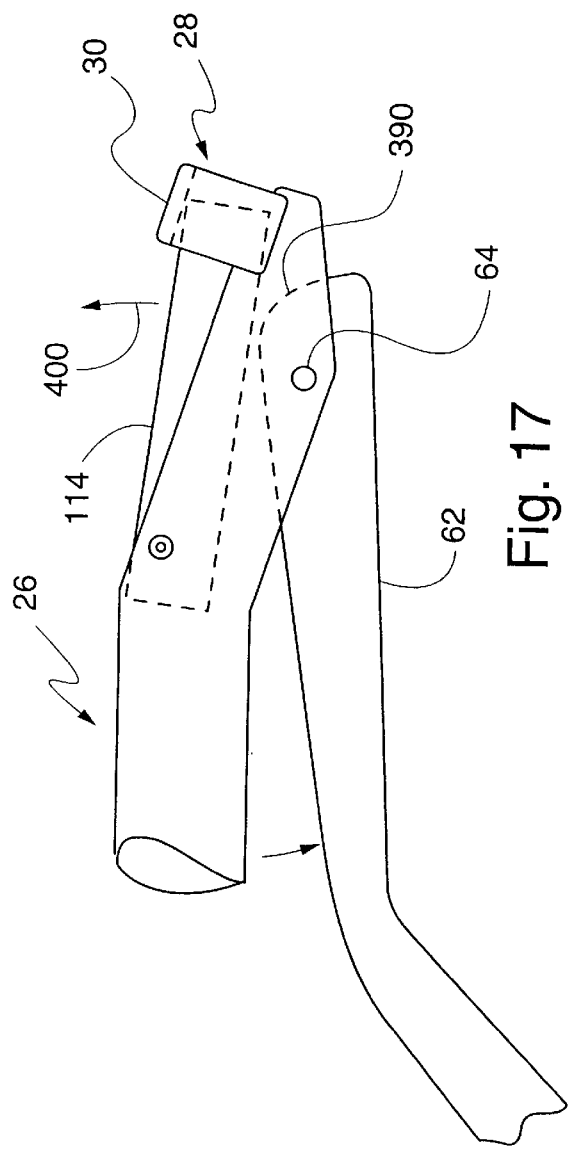
FIG. 17 is a side view of a portion of a ligation tool for the present invention, wherein the grommet crimping lever 62 has a smooth cammed upper surface 390 for use in crimping a grommet 32.

FIG. 17 provides an alternative embodiment of the assembly for crimping a grommet 32. That is, instead of the lever 62 having an upper surface for contacting the crimping bar 114, wherein this surface is substantially straight or planar, as for example shown in FIG. 2, the present embodiment has an upper surface 390 that is curved or cammed for smoother, more even application of user leverage when crimping the grommet 32.

Figure 18:
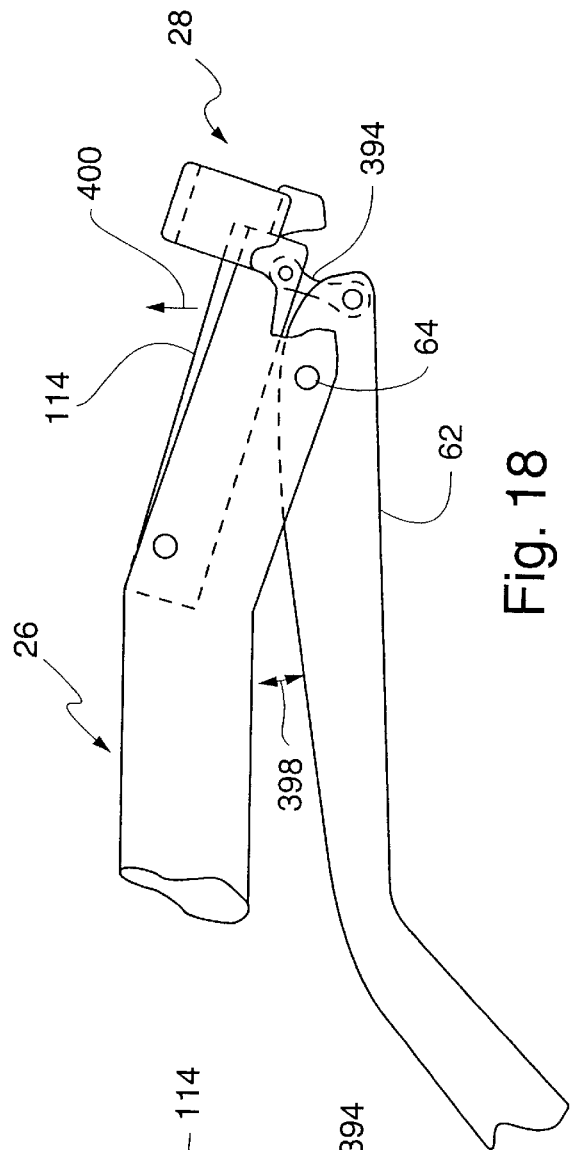
FIG. 18 illustrates another embodiment of a mechanism for crimping a grommet 32, wherein the lever 62 does not directly contact the crimping bar 114 as in FIG. 17. Instead, a link piece 394 connects the lever 62 and crimping bar 114 for crimping a grommet 32.
Figure 19:
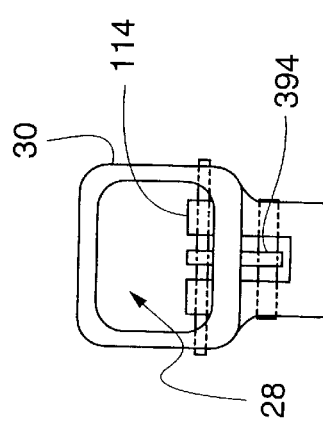
FIG. 19 is an end view of the second end portion 26 shown in FIG. 18.

FIGS. 18 and 19 show another embodiment of the crimping assembly for apparatus 10. The primary difference between the present embodiment and the embodiment of FIG. 17 is that there is a linkage piece 394 that links the lever 62 to the crimping bar 114 so that as the lever 62 is pivoted in the direction of arrow 398, the linkage piece 394 causes the crimping bar 114 to move upwardly in the direction of the arrow 400 thereby crimping a grommet 32 residing in the passageway 28.

Figure 20:
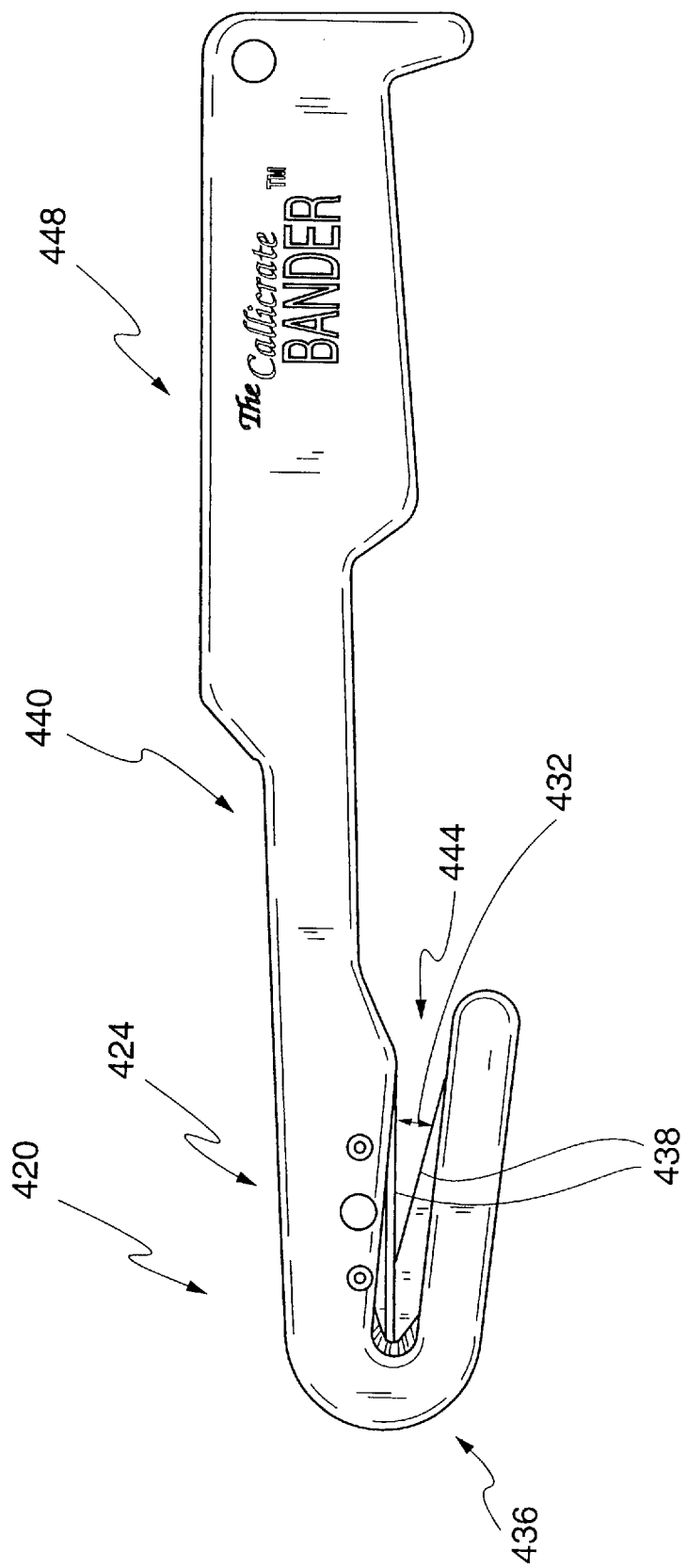
FIG. 20 shows a cutting tool useful with some embodiments of the ligation tool of the present invention, wherein the cutting tool cuts the endless elastomeric loop once its surrounding grommet 32 has been crimped.

In various embodiments of the ligation apparatus 10, a cutting tool is desired for cutting the ligating loop after the grommet 32 has been crimped. Accordingly, in FIG. 20, an embodiment of a separate cutting tool 490 is illustrated that is particularly useful for cutting the elastomeric material from which ligating loops 100 are composed. Accordingly, the cutting tool 420 has a cutting end 424 with two cutting edges 428 that have an acute angle 432 therebetween, and wherein the cutting edges are substantially enclosed within a U-shaped body 436 that is integral with the main body 440 of the cutting tool. Note that an important aspect of the cutting tool 420 is that the opening 444 for receiving the portion of the ligating loop to be cut is narrow enough so that a user's fingers are inhibited from accidentally coming in contact with the cutting edges 428. Additionally, the cutting tool 420 includes a handle 448 for grasping the cutting tool when used for severing the loop elastomeric material once the grommet 32 is crimped. Note that with the exception of the cutting edges 428 the remainder of the cutting tool 420 can be one integral piece of molded plastic, and therefore the cutting tool 420 can be inexpensively manufactured.

Figure 21:
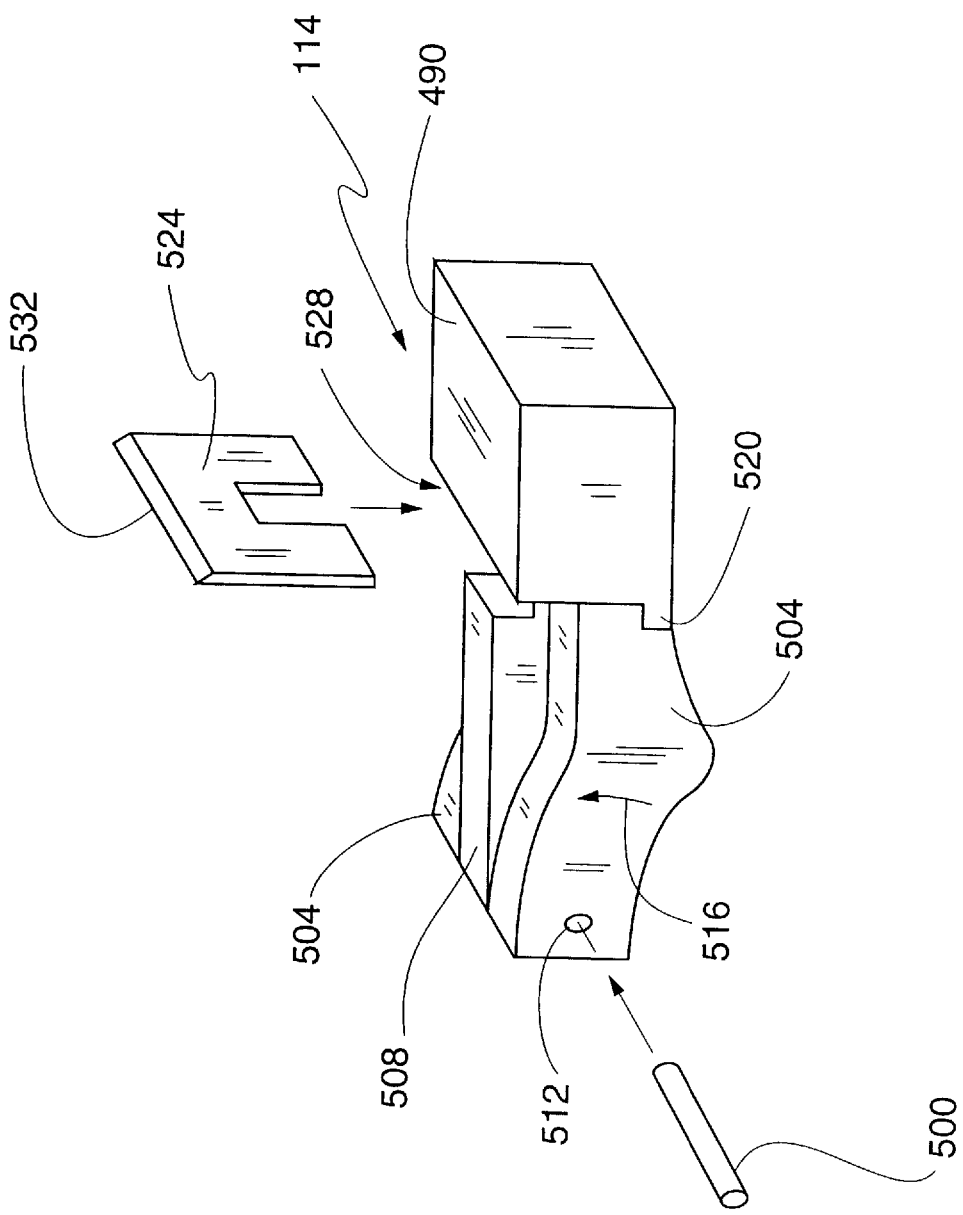
FIG. 21 shows an alternative embodiment of the crimping bar 114, wherein this embodiment is useful in an embodiment of the ligation tool that cuts the elastomeric loop after its associated grommet 32 has been crimped by continued pivoting of the lever 62.
Figure 22:
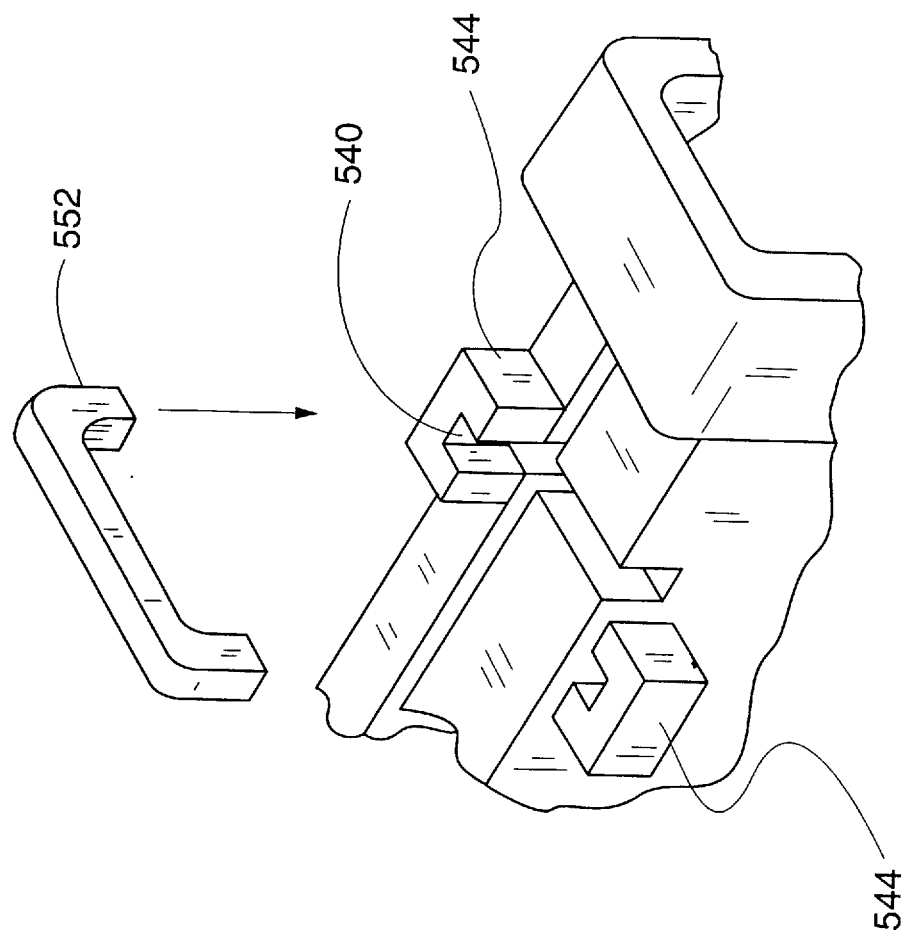
FIG. 22 is a perspective view of the crimping bar embodiment of FIG. 21 and the additional components used for providing a passageway in which an elastomeric loop is cut once its associated grommet 32 is crimped.
Figure 23:
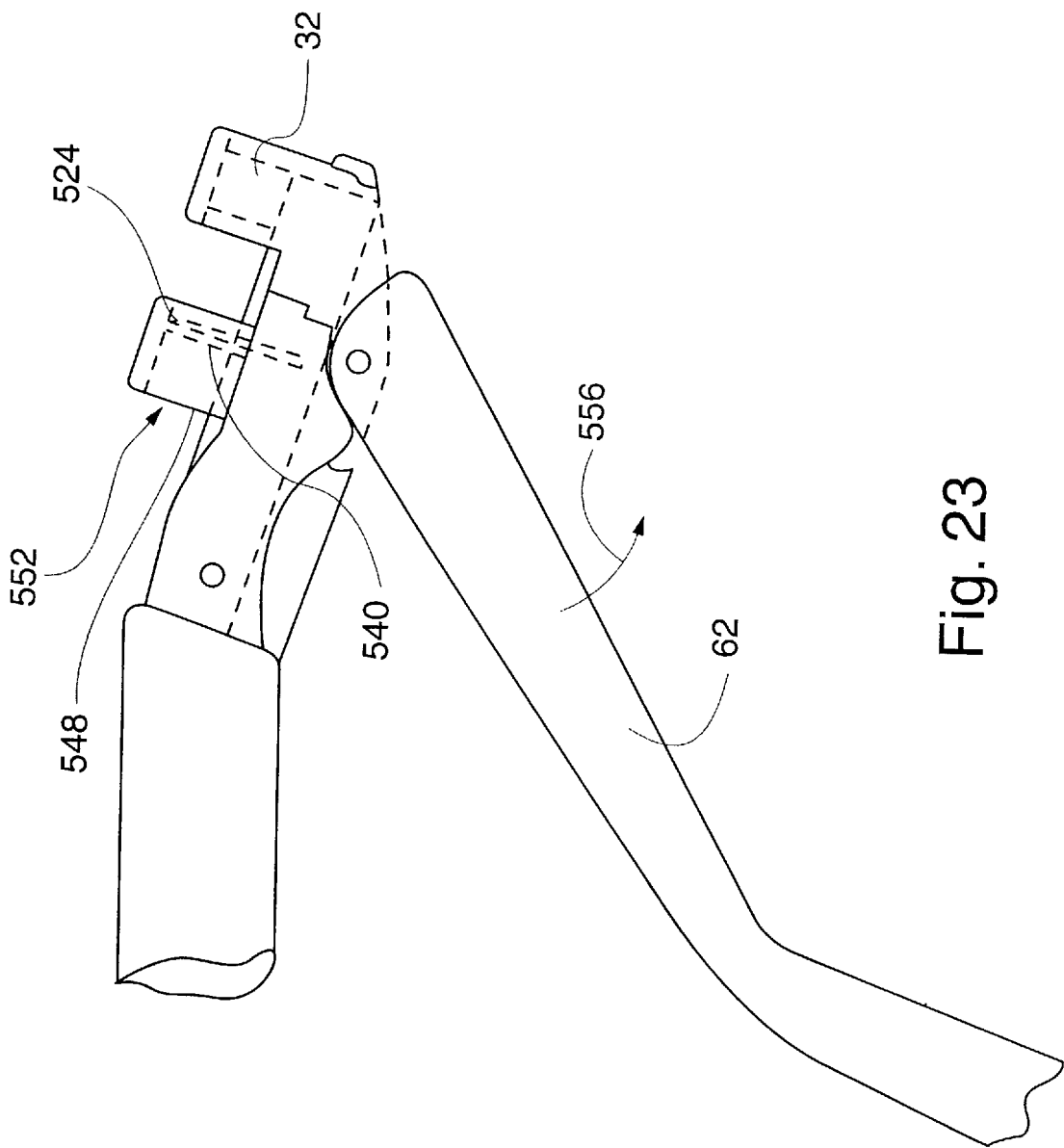
FIG. 23 is a side view of a portion of an embodiment of a ligation tool for the present invention, wherein this portion illustrates the interaction between the crimping bar 114 embodiment of FIG. 21 with the lever 62 for cutting the elastomeric loop after its associated grommet 32 has been crimped.

Referring now to FIGS. 21 through 23, a mechanism for cutting the excess loop material after the crimping of the grommet 32 is illustrated, wherein the cutting mechanism is integral with the apparatus 10 and is automatically activated with the movement of the lever 62 so that this movement both crimps the grommet 32 and cuts the elastomeric material of the ligating loop. Accordingly, FIG. 21 shows an alternative embodiment of the crimping bar 114 that may be used in the present embodiment of apparatus 10 that both crimps the grommet 32 and cuts the loop elastomeric material after the grommet has been crimped. The crimping bar 114, shown here has a crimping surface 490 that is substantially similar to previous embodiments, wherein this surface contacts a grommet 32 in the passageway 28 (e.g., FIG. 16). At the opposite end of the crimping bar 114 where this bar is pivotally attached to the remainder of the apparatus 10 via a rivet or pivot rod 500, are two cutting bars 504 on each side of a reduced width portion 508 of the crimping bar 114. Accordingly, the rivet or pivot rod 500 is provided through the bore 512 extending through the cutting bars 504 and the reduced width portion 508 for thereby pivotally attaching these components to the apparatus 10 in the same manner as the crimping bar 114 was attached in previous embodiments. Thus, the cutting bars 504 have substantial latitude for pivoting in the direction of arrow 516 but are restricted in their opposite direction due to corresponding ledge 520 abutting each cutting bar 504 (only one of which is shown), wherein the ledges are extensions of the crimping bar 114. Additionally, this cutting and crimping assembly further includes a blade 524 that is received into a slot 528 in the crimping bar 114 so that when the blade 524 is fully engaged into the slot 528, the blade edge 532 does not project outside of the slot 528. Moreover, since the blade 524 is somewhat wider than the crimping and cutting assembly, when it is provided within the slot 528, its side edges 536 are received into aligning slots 540 (FIG. 22) of sides 544 a cutting passageway 548 (FIG. 23) that has a detachable cap 552. That is, the cap 552 and the sides 544 (having the aligning slots 540) can be assembled to form the cutting passageway 548.

In operation, as indicated in FIG. 23, once the grommet 32 has been effectively crimped, further rotating of the lever 62 in the direction 556 causes the lever to come in contact with the cutting bars 504, thereby causing them to pivot about the pivot rod 500 so that the blade edge 532 enters the cutting passageway 552 and cuts the excess elastomeric loop material.

Figure 24:
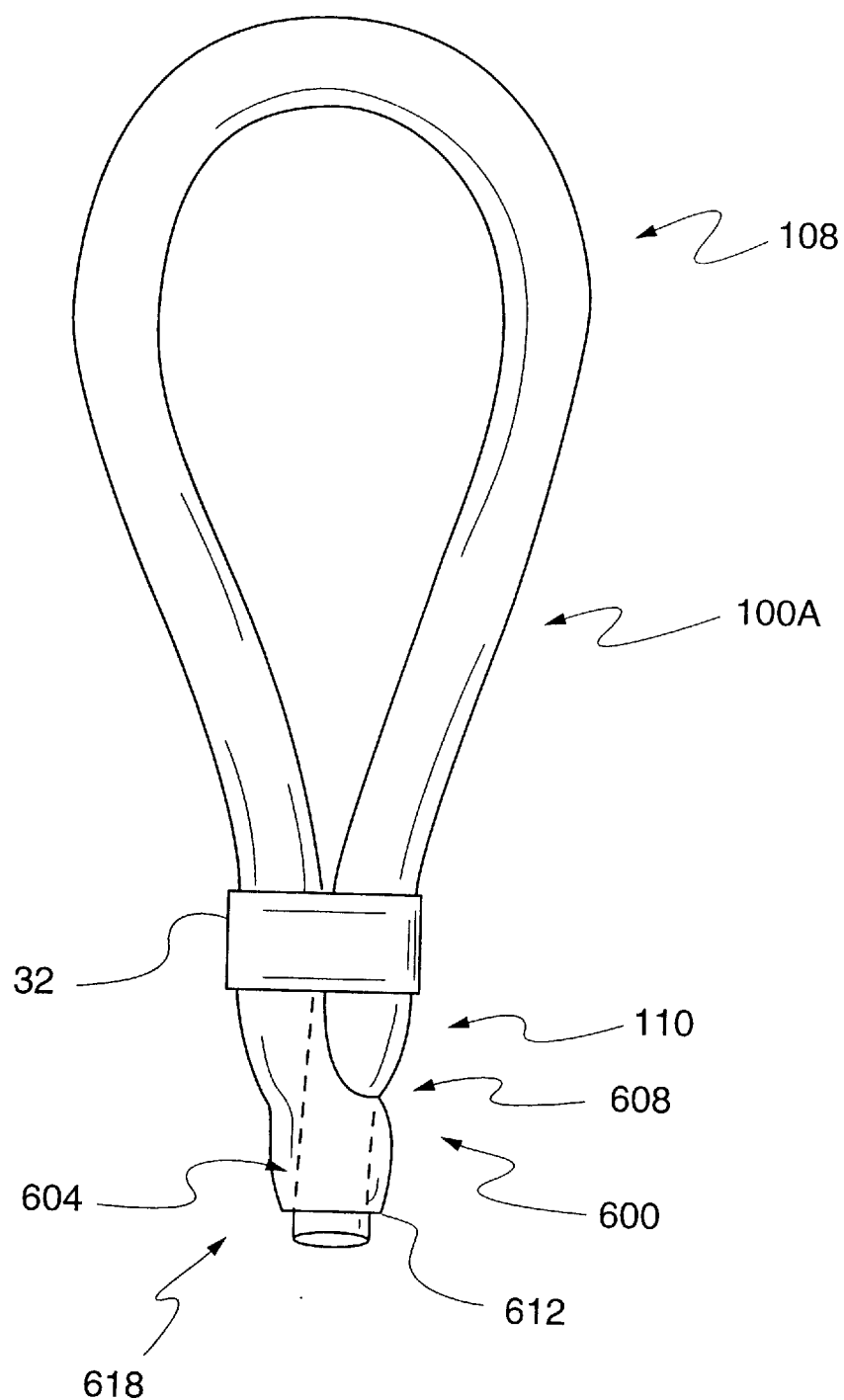
FIG. 24 is another embodiment of an endless elastomeric loop and attached grommet for the present invention.

The present invention also includes a further novel embodiment of a preformed elastomeric loop to be used with an embodiment of the apparatus 10. That is, a preformed loop 100A as shown in FIG. 24 has a length of elastomeric material with its ends joined together by fitting one end through a passageway provided in a thickness of elastomeric material substantially at the other end of the elastomeric material. That is, at a first end 600 of the elastomeric material, a passageway 604 is provided, wherein this passageway has a first opening 608 in the side of the elastomeric material and a second opening 612 through substantially the center of the cross section of the first end 600. Thus, by expanding the passageway 604, the second end 618 of the elastomeric material can be inserted through the passageway 604 so that the elastomeric material surrounding the passageway constricts about the portion of the second end 618 that is within the passageway and thereby firmly holds the second end 618 so that the loop 100A is formed. More precisely, a plurality of clustered projections are inserted into the center of the cross section of the first end 600 and caused to protrude out the side of the elastomeric material at the first opening 608. Subsequently, the projections are spread apart thereby creating the passageway 604 through which the second end 618 is passed through. Thus, upon removing the projections, the passageway 604 constricts about the portion of the elastomeric material in the passageway 604. It is important to note that the elastomeric material utilized for ligation loops such as 100A, constricts tightly enough about the portion of the elastomeric material in the passageway 604 so that the loop ends 600 and 618 do not separate. In particular, during the initial tensioning provided on the loop for the beginning stages of the winding process (i.e., prior to the elastomeric material wrapping about itself on the winding assembly 14), the second end 618 does not retract through the passageway 604. Note that when the loop has wrapped back upon itself on the winding assembly 14, there is substantially no further increase in tension for inducing a separation of the loop ends 600 and 68. Further note that since neither the exterior surface of the elastomeric material nor the interior surface of the passageway 608 are lubricated, there is a high coefficient of friction therebetween. Accordingly, the present loop embodiment is capable of sustaining a tension in the range of 90 to 150 pounds without breaking or otherwise failing.

Figure 14:
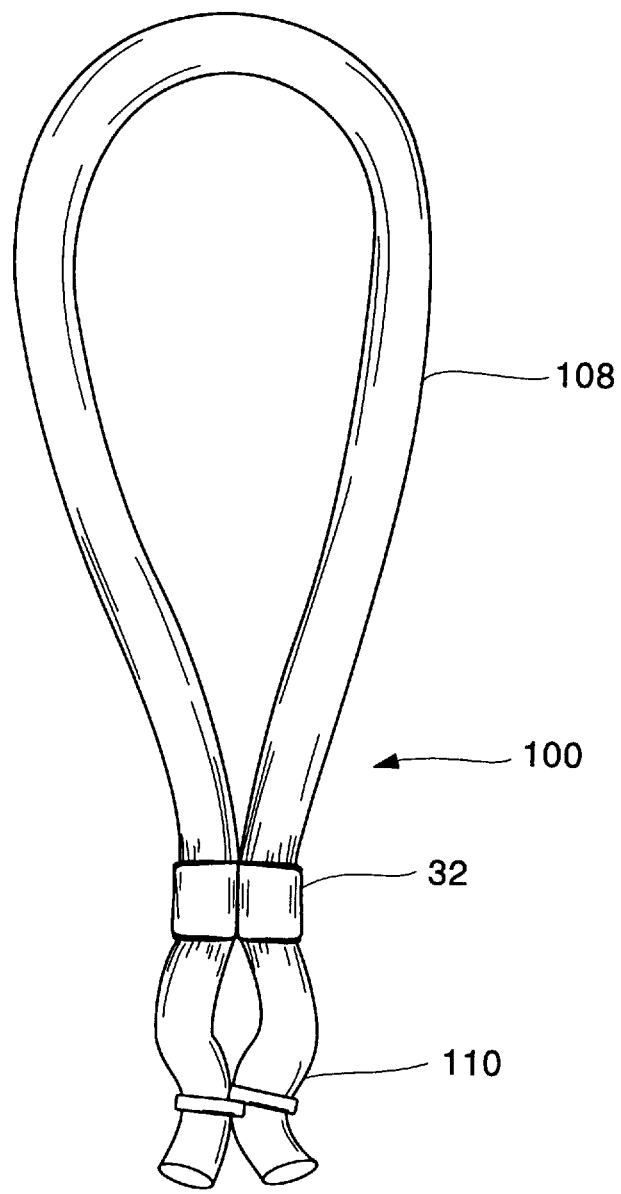
FIG. 14 shows a plan view of an alternative embodiment of the endless elastomeric loop and attached grommet.
Figure 15:
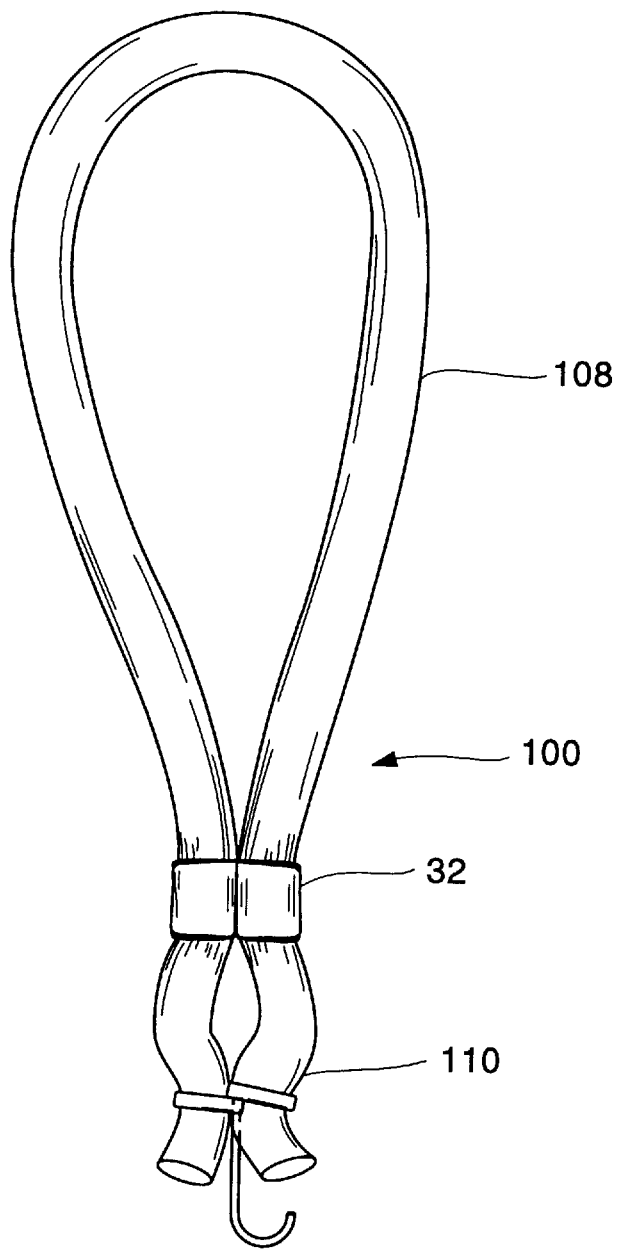
FIG. 15 shows yet another embodiment of the endless elastomeric loop and attached grommet.

Thus, once formed, the preformed loop 100A is inserted through a grommet 32 as shown in this figure so that a ligation band is provided that functions identically to those described in FIGS. 13 through 15, yet without an additional tying band such as in FIGS. 14 and 15.

II. Cattle Raising Management Program

Figure 25:
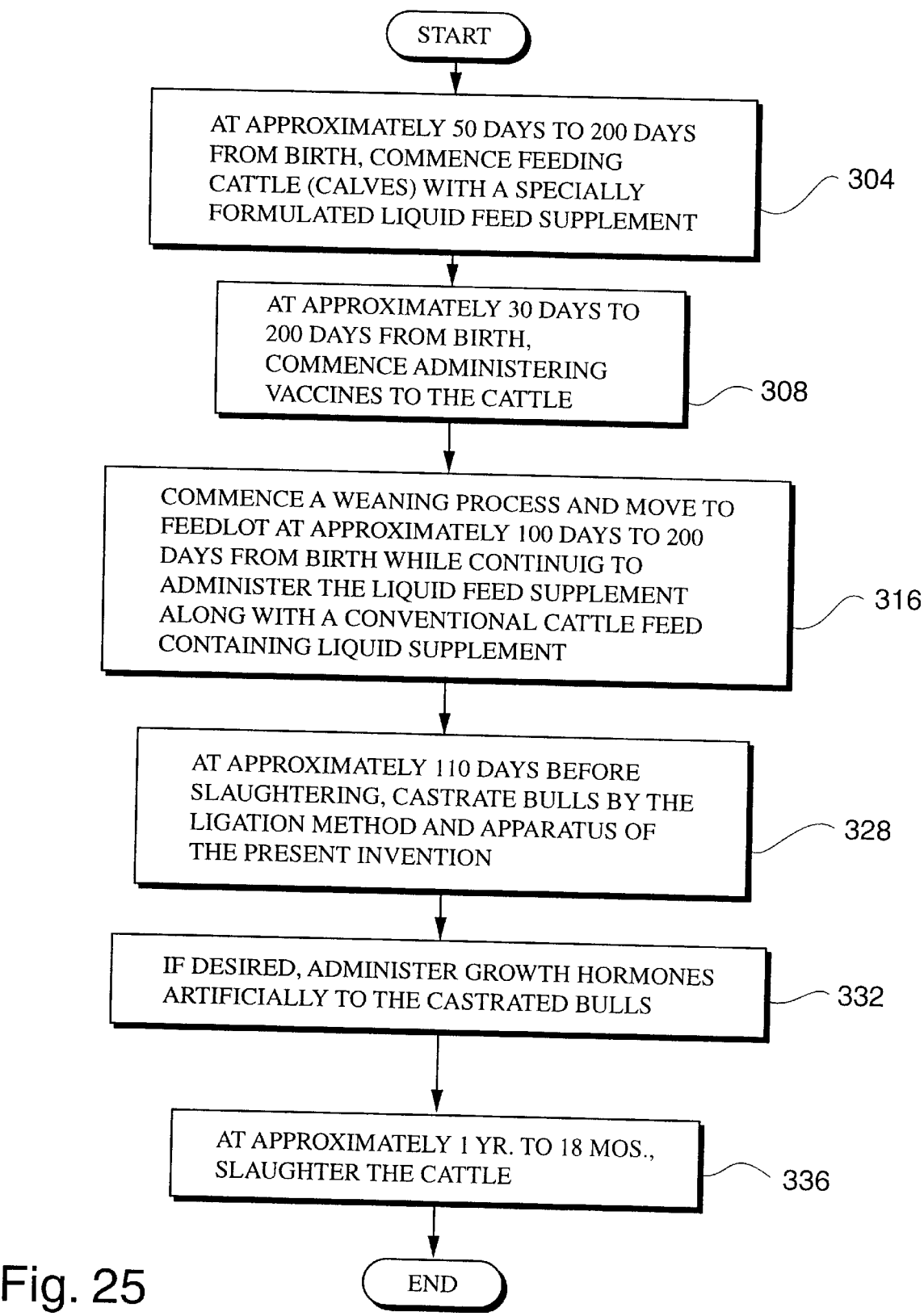
FIG. 25 shows a flow chart of the steps of the cattle raising management program aspect of the present invention.

In FIG. 25, the steps are provided for a cattle raising management program that preferably utilizes the ligation apparatus 10 described hereinabove. In particular, the steps of the cattle raising management program induce accelerated growth in cattle whereby they may be slaughtered substantially earlier than in conventional cattle raising methods. Essentially, the cattle raising management program of FIG. 25 is a program for the early weaning of calves, the late castration of bulls, preventative health care and consistent provision of a high quality nutritional feed supplement. Further, the feed supplement is nutritious as well as distinctive enough so that variations in cattle feed do not substantially affect the feeding habits of the cattle.

Accordingly, in step 304 at approximately 50 days to 200 days from birth, preferably 100 to 150 days from birth, the above-mentioned liquid feed supplement is provided to the calves prior to commencement of weaning. Note that in one formulation of the liquid feed supplement, it is formulated from fat stock, glutamate fermentation extract, corn distillers solubles and corn steepwater. More particularly, the feed supplement includes corn condensed distillers solubles, corn steep liquor, vegetable fat and protoferm. Accordingly, this feed supplement includes protein in the range of 12% to 18%, and more precisely, approximately 16% protein, of which approximately 56% is natural, with the remaining protein being in the form of ammonium chloride. Additionally, the supplement has approximately 10% fat that can meet the optimum dietary levels for fat when used as a feed conditioner. Accordingly, on a dry matter basis, the level of energy and protein substantially exceeds that of #2 yellow corn. Note that in addition to the composition of the supplement, it is believed that the supplement should have a distinctive odor that is recognizable by the cattle being raised. Accordingly, providing this liquid supplement to non-weaned calves and subsequently providing the same supplement with conventional cattle feed allows for a smoother, less stressful transition when the cattle are weaned. A supplement satisfying this description is provided by Timberlake Transportation and Transfer, Inc. of Springfield, Ill. and is sold under the product name "MIX 30".

In step 308, as preparation for weaning, vaccinations are also administered to the calves so that any weakening of their immune system due to early weaning is mitigated by the vaccinations. In step 316, a progressive weaning process is commenced at approximately 4 to 6 months after birth. Note that during this weaning process, the liquid feed supplement and the vaccinations are continued to be administered to the calves. However, the calves are also progressively weaned from their intake of the liquid feed supplement as a liquid and instead provided with a feed that has been sprayed or otherwise coated with the supplement (e.g., conventional feed is combined with "Mix-30"). In the feedlot the calves are provided with a cattle feed having applied thereto the feed supplement to which they have now grown accustomed. Accordingly, by applying this feed supplement to all cattle feed in the feedlot, the nutritional value of the cattle feed is not only enhanced, but there also appears to be a general reduction in stress in the cattle. It is thus believed that the addition of the feed supplement induces the cattle to commence feeding at the feedlot more readily than is typical of conventional techniques for raising cattle. Note that to further reduce stress, the young calves are aided in becoming familiarized with the feedlot surroundings by the placing, in the feedlot itself, of a feeding bin or container that is the same or identical to the container used for feeding in the pasture. Additionally, the bin is preferably provided with the liquid feed supplement used in the pasture. In addition, the liquid feed is combined with more conventional feed, such as hay and/or grain, so that the smell and taste of the conventional feed is similar to the liquid feed to which the young calves are now accustomed. In this manner, significant improvements in weight gain of young calves is made possible since the calves are more inclined to eat. Moreover, the stress typically experienced by young cattle when moved away from their mothers and into a feedlot is significantly reduced due to the familiar sights, smells and tastes of feed provided by the present invention. The present inventors have noted weight gain of cattle as being approximately three pounds per day for the first three weeks after moving the cattle to a feedlot. This compares with an absence of any gain in weight by similarly situated animals using conventional cattle raising techniques. Moreover, due to the lack of stress encountered by such young calves, the incidents of sickness and illness is significantly decreased. As such, the present invention can be viewed as a method for improving the wellness of young cattle during a transition from liquid feed supplements to solid food, while at the same time increasing the weight gain of such animals during this time period.

It is important to note that the present cattle raising management program provided herein does not castrate bulls until approximately 80–120 days and more preferably about 110 days before slaughter. Thus, the bulls grow substantially more rapidly than if they are castrated earlier. In fact, a 10–15% improvement in feed conversion (i.e., pounds of feed per pound of meat produced) is not uncommon utilizing the present invention. Accordingly, in step 328, bulls are castrated at approximately 80–120 days and more preferably about 110 days before slaughtering using the ligation method and apparatus of the present invention. Further, the ligation method and novel apparatus disclosed herein, is substantially less stressful and safer than other forms of castration. Conventional practices teach away from late stage (e.g., after about 6 months of age) castration due to the stress typically encountered by such older animals. This stress caused such animals to reduce or cease their eating frequency and amount of food consumption, resulting in a significant reduction in desired weight gain. The present inventors have discovered that by using the novel method and apparatus of the present invention, late stage castration does not present the stress, and the accompanying reduction in food consumption (and hence growth), experienced using conventional castration methods. Additionally, as an infection preventative measure, a disease preventative vaccination is administered to each bull about the time of castration. In particular, this vaccination may be for one or more of tetanus, bovine statistical virus, red nose, BVD Pasteurella, lepto and blackleg. Following castration as indicated in step 332, growth hormones may be artificially administered (if deemed desirable) to the castrated bulls to enhance continued growth without the undesirable effects of further masculinity that would be manifested if the bulls were not castrated. Finally, in step 336, at approximately one year to eighteen months after birth, preferably at about one year, the cattle may be slaughtered since they will have reached a size wherein it is economical to slaughter them and their meat will be of superior quality. The cutability of these animals is significantly increased, as demonstrated by improved lean-to-fat ratios.

It is important to note that for conventional cattle raising practices, the slaughtering of the cattle within 12 months–18 months from birth is typically only performed under abnormal circumstances due to the fact that the cattle have not gained sufficient size to make it cost effective to slaughter them. However, with the accelerated growth that occurs due to the steps of FIG. 25, the cattle may be slaughtered six months to a year earlier than would be the case if a conventional cattle raising management method were utilized.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. A method of raising bulls, comprising:
   commencing a weaning process at about 100 to 200 days after the birth of a bull;
   providing said bull with a feed supplement; and
   castrating said bull within at least 110 days from slaughter using a preformed endless loop of elastomeric ligature material.

2. A method, as claimed in claim 1, wherein approximately 50% of said protein of said feed supplement is comprised of natural protein.

3. A method, as claimed in claim 1, wherein said feed supplement is a liquid provided to said bull during weaning.

4. A method, as claimed in claim 1, further including a step of feeding said bull in a feedlot, said feedlot provided with a bin containing said feed supplement in addition to conventional feed combined with said feed supplement.

5. A method, as claimed in claim 4, wherein said step of feeding includes spraying said food supplement onto conventional cattle feed.

6. A method, as claimed in claim 4, wherein said conventional cattle feed comprises hay and/or grain.

7. A method, as claimed in claim 1, further including a step of slaughtering said bull approximately one year to 18 months after birth.

8. A method, as claimed in claim 1, further including a step of administering growth enhancing promotants after said step of castrating.

9. A method of raising bovines, comprising:
   commencing a progressive weaning process of a bovine at about 50 to about 200 days after birth;
   providing a liquid feed supplement to said bovine, said supplement being sprayed onto conventional cattle feed when said bovine first starts eating conventional feed;
   slaughtering said bovine approximately one year to 18 months after birth.

10. A method, as claimed in claim 9, wherein said feed supplement comprises vegetable fat, glutamate fermentation extract, corn steeped liquor, and corn condensed distillers solubles.

11. A method, as claimed in claim 9, wherein said progressive weaning extends approximately 30 days from birth.

12. A method, as claimed in claim 9, wherein said step of commencing includes vaccination of said bovine as a disease preventative measure.

13. A method, as claimed in claim 9, wherein said bovine is weaned using a liquid feed supplement that comprises approximately 16% protein and 10% fat.

14. A method, as claimed in claim 9, wherein said feed supplement has a distinctive odor.

15. A method of raising cattle, comprising:
   castrating bulls of said cattle at approximately 5 months to approximately 14 months of age, wherein said step of castrating is performed by ligation; and
   slaughtering said cattle approximately one year to 18 months after birth.

16. A method, as claimed in claim 15, wherein said bulls are weaned using a liquid feed supplement that comprises approximately 15% protein and 10% fat.

17. A method, as claimed in claim 16, wherein said liquid feed supplement is sprayed onto conventional cattle feed when said bulls first start eating conventional feed.

18. A method, as claimed in claim 16, wherein said feed supplement has a distinctive odor and taste.

19. A method, as claimed in claim 15, further including a step of administering a disease preventative composition to said cattle.

20. A method, as claimed in claim 19, wherein said disease preventative composition is effective to treat a disease selected from the group consisting of tetanus, bovine statical virus, red nose, BVD Pasturella, lepto and blackleg.

21. A method of raising bulls, comprising:
   delaying the castration of bulls until approximately 5 months to approximately 14 months after the birth of said bulls, wherein said step of castrating is performed by a ligation method that does not cause said animal to lose more than about 15 pounds of weight subsequent to said castration step.

* * * * *

UNITED STATES PATENT AND TRADEMARK OFFICE
CERTIFICATE OF CORRECTION

PATENT NO. : 5,843,095
DATED : December 1, 1998
INVENTOR(S) : Callicrate

It is certified that error appears in the above-identified patent and that said Letters Patent is hereby corrected as shown below:

delete all language in Claim 1 and replace it with the following:

1. A method of raising and castrating bulls, comprising:
commencing a weaning process at about 100 to 200 days after the birth of a bull;
providing said bull with a feed supplement;
castrating said bull within at least 110 days from slaughter, wherein steps of castrating said bull comprise:
attaching a preformed endless loop of elastomeric ligature material to a ligation tool, wherein said endless loop has a forward portion and a rearward portion;
manually passing said forward portion about said bull's scrotum;
pulling said loop using said tool to tighten said loop around said scrotum; and
attaching a grommet between said forward portion and said rearward portion, wherein when said grommet is deformed, said grommet secures said forward portion about said scrotum and inhibits blood flow by maintaining pressure around said scrotum of the bull.

In Claim 2, line 1, please change "A" to "The". In line 2, please delete "said protein" and insert therefor -- a protein --.

UNITED STATES PATENT AND TRADEMARK OFFICE
CERTIFICATE OF CORRECTION

PATENT NO. : 5,843,095
DATED : December 1, 1998
INVENTOR(S) : Callicrate

It is certified that error appears in the above-identified patent and that said Letters Patent is hereby corrected as shown below:

In Claim 3, line 1, please delete "A" and insert therefor -- The --.

In Claim 4, line 1, please delete "A" and insert therefor -- The --; in lines 3 and 4, please delete "in addition to conventional feed combined with said feed supplement" and insert therefor -- and a cattle feed --.

In Claim 5, line 1, please delete "A" and insert therefor -- The --; on lines 2 and 3, please delete "conventional" and insert therefor -- said --.

In Claims 6, 7 and 8, line 1, please delete "A" and insert therefor -- The --.

Please delete all language in Claim 9 and replace it with the following:

9. A method of raising and castrating bovines, comprising:
commencing a progressive weaning process of a bovine at about 50 to about 200 days after birth;
providing a liquid feed supplement to said bovine, said supplement being sprayed onto a cattle feed when said bovine first starts eating said feed;
castrating said bovine before slaughtering, wherein said steps of castrating said bovine comprising:

UNITED STATES PATENT AND TRADEMARK OFFICE
CERTIFICATE OF CORRECTION

PATENT NO.  :  5,843,095
DATED       :  December 1, 1998
INVENTOR(S) :  Callicrate It is certified that error appears in the above-identified patent and that said Letters Patent is hereby corrected as shown below:

attaching a preformed endless loop of elastomeric ligature material to a ligation tool, wherein said endless loop has a forward portion and a rearward portion;

manually passing said forward portion about said bull's scrotum;

pulling said loop using said tool to tighten said loop around said scrotum; and slaughtering said bovine approximately one year to 18 months after birth; and attaching a grommet between said forward portion and said rearward portion, wherein when said grommet is deformed, said grommet secures said forward portion about said scrotum and inhibits blood flow by maintaining pressure around said scrotum of the bull.

In Claims 10-13, line 1, please delete "A" and insert therefor -- The --.

In Claim 14, line 1, please delete "A" and insert therefor -- The --; in line 2, please delete "a distinctive" and insert therefore -- an --.

Please delete all the language in Claim 15 and replace it with the following:

15. A method of raising and castrating cattle, comprising:

UNITED STATES PATENT AND TRADEMARK OFFICE
CERTIFICATE OF CORRECTION

PATENT NO. : 5,843,095
DATED : December 1, 1998
INVENTOR(S) : Callicrate

It is certified that error appears in the above-identified patent and that said Letters Patent is hereby corrected as shown below:

castrating bulls of said cattle at approximately 5 months to approximately 14 months of age, wherein steps of castrating comprising:
        attaching a preformed endless loop of elastomeric ligature material to a ligation tool, wherein said endless loop has a forward portion and a rearward portion;
        manually passing said forward portion about said bull's scrotum for inhibiting blood flow by maintaining pressure around said scrotum of the bull before ligating the bull, wherein said grommet deforms when said grommet secures said forward portion about said scrotum;
        pulling said loop using said tool to tighten said loop around said scrotum;
        attaching a grommet between said forward portion and said rearward portion, wherein when said grommet is deformed, said grommet secures said forward portion about said scrotum and inhibits blood flow by maintaining pressure around said scrotum of the bull; and
        slaughtering said cattle approximately one year to 18 months after birth.

In Claim 16, line 1, please delete "A" and insert therefor -- The --.
    In Claim 17, line 1, please delete "A" and insert therefor -- The --; on line 2, please delete "conventional" and insert therefor -- a --; on line 3, please delete "conventional" and insert therefor -- said --.

UNITED STATES PATENT AND TRADEMARK OFFICE
CERTIFICATE OF CORRECTION

PATENT NO. : 5,843,095
DATED : December 1, 1998
INVENTOR(S) : Callicrate

It is certified that error appears in the above-identified patent and that said Letters Patent is hereby corrected as shown below:

In Claim 18, line 1, please delete "A" and insert therefor -- The --; on line 2, please delete "a distinctive odor and taste" and insert therefor -- an odor --.

In Claims 19 and 20, line 1, please delete "A" and insert therefor -- The --.

Please delete all the language in Claim 21 and replace it with the following:

21. A method of raising and castrating bulls, comprising:

delaying the castration of the bulls until approximately 5 months to approximately 14 months after the birth of the bull, wherein steps of castrating comprises:

attaching a preformed endless loop of elastomeric ligature material to a ligation tool, wherein said endless loop has a forward portion and a rearward portion;

attaching a grommet between said forward portion and said rearward portion;

manually passing said forward portion about said bull's scrotum for inhibiting blood flow by maintaining pressure around said scrotum of the bull before ligating the bull, wherein said grommet deforms when said grommet secures said forward portion about said scrotum; and pulling said loop using said tool to tighten said loop around said scrotum;

UNITED STATES PATENT AND TRADEMARK OFFICE
CERTIFICATE OF CORRECTION

PATENT NO. : 5,843,095
DATED : Dec. 1, 1998
INVENTOR(S) : Callicrate

It is certified that error appears in the above-identified patent and that said Letters Patent is hereby corrected as shown below:

whereby said castration steps do not cause the bulls to lose more than 15 pounds of weight subsequent to said castration steps.

Signed and Sealed this

Tenth Day of August, 1999

Attest:

Attesting Officer

Q. TODD DICKINSON

Acting Commissioner of Patents and Trademarks

UNITED STATES PATENT AND TRADEMARK OFFICE
CERTIFICATE OF CORRECTION

PATENT NO.   : 5,843,095
DATED        : December 1, 1998
INVENTOR(S)  : Callicrate It is certified that error appears in the above-identified patent and that said Letters Patent is hereby corrected as shown below:

Column 1,
Line 50, "4,527,179" should read -- 4,572,179 --.

Signed and Sealed this

Fourteenth Day of January, 2003

JAMES E. ROGAN
*Director of the United States Patent and Trademark Office*